(12) United States Patent
Fukiage

(10) Patent No.: US 11,496,662 B2
(45) Date of Patent: Nov. 8, 2022

(54) IMAGE PROCESSING APPARATUS, IMAGE PROCESSING METHOD, AND IMAGE PICKUP SYSTEM FOR DISPLAYING INFORMATION ASSOCIATED WITH AN IMAGE

(71) Applicant: SONY CORPORATION, Tokyo (JP)

(72) Inventor: Chihiro Fukiage, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 16/619,136

(22) PCT Filed: Jun. 11, 2018

(86) PCT No.: PCT/JP2018/022258
§ 371 (c)(1),
(2) Date: Dec. 4, 2019

(87) PCT Pub. No.: WO2018/230510
PCT Pub. Date: Dec. 20, 2018

(65) Prior Publication Data
US 2020/0099847 A1 Mar. 26, 2020

(30) Foreign Application Priority Data
Jun. 13, 2017 (JP) .............................. JP2017-116340

(51) Int. Cl.
*H04N 5/225* (2006.01)
*H04N 5/232* (2006.01)

(52) U.S. Cl.
CPC ..... *H04N 5/23203* (2013.01); *H04N 5/23216* (2013.01)

(58) Field of Classification Search
CPC .................................................. H04N 5/23203
See application file for complete search history.

(56) References Cited

U.S. PATENT DOCUMENTS

| | | | |
|---|---|---|---|
| 2003/0135845 A1* | 7/2003 | Nunomura | G06F 9/30185 717/136 |
| 2005/0108162 A1* | 5/2005 | Sugihara | G06T 11/60 705/40 |

(Continued)

FOREIGN PATENT DOCUMENTS

| | | |
|---|---|---|
| CN | 104919790 A | 9/2015 |
| CN | 108028884 A | 5/2018 |

(Continued)

OTHER PUBLICATIONS

Extended European Search Report of EP Patent Application No. 18816815.7, dated May 29, 2020, 08 pages.

(Continued)

*Primary Examiner* — Gary C Vieaux
(74) *Attorney, Agent, or Firm* — Chip Law Group

(57) ABSTRACT

The display of information associated with a particular position of a picked-up image is enabled. Image data is transmitted to external equipment. Instruction information regarding the image data is received from the external equipment. A display-use image reflecting the instruction information is generated on the basis of the instruction information. For example, the display-use image is generated by displaying details of the instruction information on an image corresponding to the image data. As another example, position information is added to the instruction information. The display-use image is then generated by displaying the details of the instruction information in an image position indicated by the position information.

19 Claims, 11 Drawing Sheets

(56) References Cited

U.S. PATENT DOCUMENTS

| | | | |
|---|---|---|---|
| 2015/0319354 A1* | 11/2015 | Ichikawa | H04N 5/232941 |
| | | | 348/211.2 |
| 2016/0269631 A1* | 9/2016 | Jiang | G09B 5/02 |
| 2017/0099425 A1 | 4/2017 | Ichikawa et al. | |
| 2018/0284966 A1 | 10/2018 | Irie | |

FOREIGN PATENT DOCUMENTS

| | | | |
|---|---|---|---|
| CN | 108495052 A | | 9/2018 |
| JP | 05-064041 A | | 3/1993 |
| JP | 2006-014119 A | | 1/2006 |
| JP | 2006014119 A | * | 1/2006 |
| JP | 2011-035866 A | | 2/2011 |
| JP | 2011035866 A | * | 2/2011 |
| JP | 5770960 B1 | | 8/2015 |
| JP | 6053877 B2 | | 12/2016 |
| JP | 6335394 B2 | | 5/2018 |
| WO | 2015/052960 A1 | | 4/2015 |
| WO | 2017/051605 A1 | | 3/2017 |

OTHER PUBLICATIONS

International Search Report and Written Opinion of PCT Application No. PCT/JP2018/022258, dated Jul. 31, 2018, 07 pages of ISRWO.

* cited by examiner

FIG.1
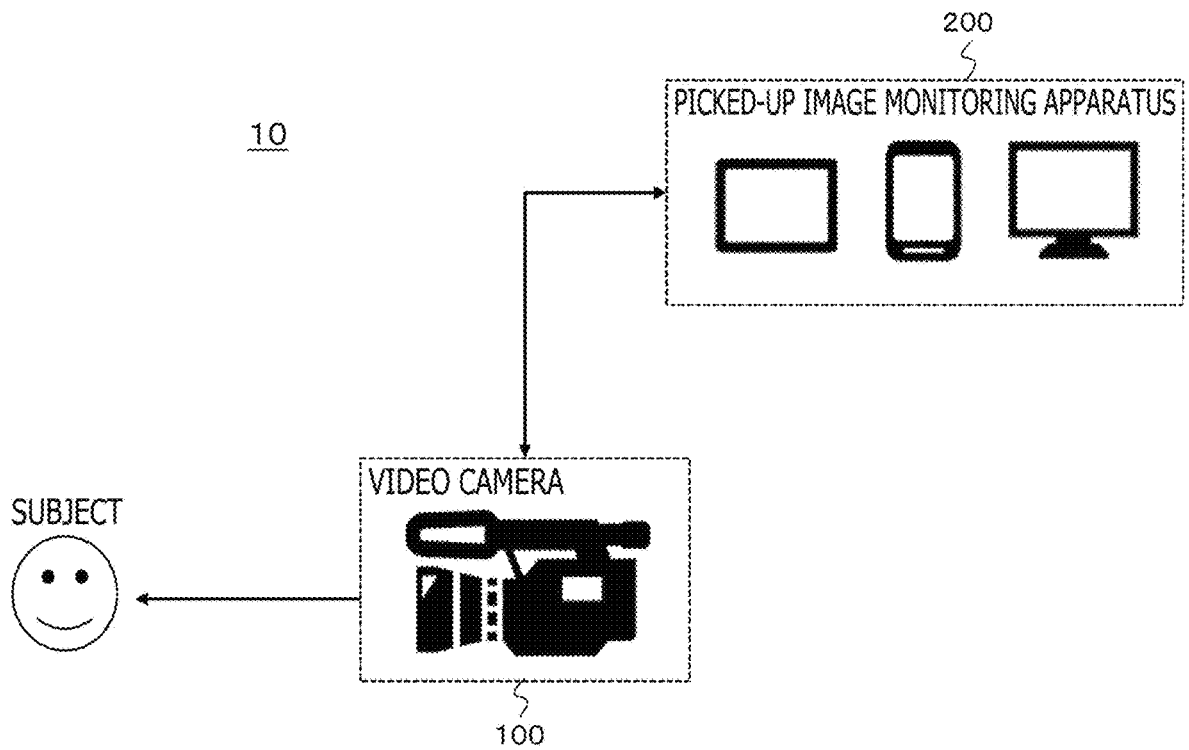
FIG.2
| ID | OPERATION | INSTRUCTION TYPE | COLOR | SHAPE | MOVEMENT |
|----|-----------|------------------|-------|-------|----------|
| 0 | NONE | | | | |
| 1 | SINGLE TAP | "point" | BLUE | CIRCLE | FIXED |
| 2 | DOUBLE TAP | "zoom out" | ORANGE | CIRCLE | FROM INSIDE TO OUTSIDE |
| 3 | LONG TAP | "zoom in" | BLUE | RECTANGLE | FROM OUTSIDE TO INSIDE |
| 4 | FLICK | "fast pan" | LIGHT BLUE | ARROW | FIXED |
| 5 | SWIPE | "slow pan" | YELLOWISH GREEN | ARROW | FIXED |
| ... | ... | ... | ... | ... | ... |
FIG.3
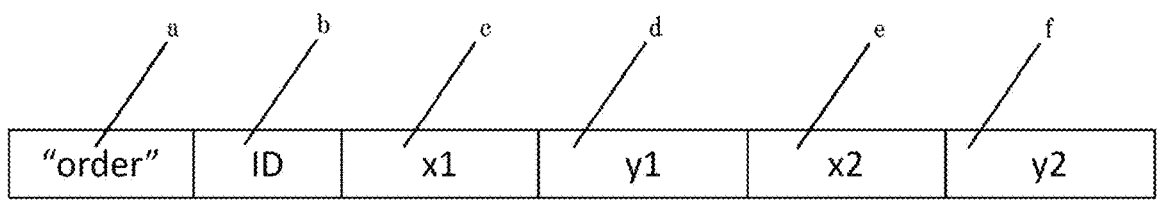

IMAGE PROCESSING APPARATUS, IMAGE PROCESSING METHOD, AND IMAGE PICKUP SYSTEM FOR DISPLAYING INFORMATION ASSOCIATED WITH AN IMAGE

CROSS REFERENCE TO RELATED APPLICATIONS

This application is a U.S. National Phase of International Patent Application No. PCT/JP2018/022258 filed on Jun. 11, 2018, which claims priority benefit of Japanese Patent Application No. JP 2017-116340 filed in the Japan Patent Office on Jun. 13, 2017. Each of the above-referenced applications is hereby incorporated herein by reference in its entirety.

TECHNICAL FIELD

The present technology relates to an image processing apparatus, an image processing method, and an image pickup system. More particularly, the technology relates to an image processing apparatus for displaying information associated with a picked-up image.

BACKGROUND ART

Heretofore, in an image pickup environment where a video camera is used, an intercom is known to be used by a monitoring person to vocally give a photographer (i.e., camera operator) image pickup instructions such as an image pickup targeting instruction, zoom-in and zoom-out instructions, and a pan instruction. In a case where such instructions are given by voice, there may conceivably be cases in which the monitoring person has difficulty in correctly conveying the details of an instruction to the camera operator.

For example, PTL 1 describes a remote control apparatus having a display unit that displays the same details as those displayed on a viewfinder screen of the video camera when menus are set on the video camera.

CITATION LIST

Patent Literature

[PTL 1]
Japanese Patent Laid-Open No. Hei 5-056326

SUMMARY

Technical Problem

An object of the present technology is to enable the display of instruction information regarding image data from external equipment.

Solution to Problem

One concept of the present technology is to provide an image processing apparatus including: a transmission unit configured to transmit image data to external equipment; a reception unit configured to receive instruction information regarding the image data from the external equipment; and a display-use image generating unit configured to generate a display-use image based on and reflecting the instruction information.

According to the present technology, the transmission unit transmits the image data to the external equipment. The reception unit receives the instruction information regarding the image data from the external equipment. The display-use image generating unit then generates a display-use image based on and reflecting the instruction information. For example, details of the instruction information may include image pickup instruction information.

As another example, the display-use image generating unit may generate the display-use image by displaying details of the instruction information on an image corresponding to the image data. As a further example, position information may be added to the instruction information, and the display-use image generating unit may generate the display-use image by displaying details of the instruction information in an image position indicated by the position information.

As another example, the display-use image generating unit may generate the display-use image having either a displayed mark or a displayed text corresponding to details of the instruction information. In this case, the display-use image generating unit may have a conversion table for obtaining either the mark or the text based on the instruction information and corresponding to the details thereof. The image processing apparatus may further include an image pickup unit configured to obtain the image data. The image processing apparatus may further include a display unit configured to display the display-use image.

According to the present technology, as outlined above, the image data is transmitted to the external equipment. The instruction information regarding the image data is received from the external equipment. The display-use image reflecting the instruction information is then generated. This enables the display of the instruction information from the external equipment regarding the image data.

Another concept of the present technology is to provide an image processing apparatus including: a reception unit configured to receive image data from external equipment; a processing unit configured to generate instruction information regarding the image data; and a transmission unit configured to transmit the instruction information to the external equipment.

According to the present technology, the reception unit receives the image data from the external equipment. The processing unit generates the instruction information regarding the image data. The transmission unit then transmits the instruction information to the external equipment. For example, details of the instruction information may include image pickup instruction information. As another example, the processing unit may have a conversion table for obtaining the instruction information based on an operation performed by a user. In this case, the image processing apparatus may further include a table setting unit configured to set the conversion table.

As yet another example, the processing unit may further generate a display-use image based on and reflecting the instruction information. In this case, the processing unit may generate the display-use image having either a displayed mark or a displayed text corresponding to details of the instruction information. Also in this case, the processing unit may have a conversion table for obtaining either the mark or the text based on the instruction information and corresponding to the details thereof.

As another example, the image processing apparatus may further include a display unit configured to display the display-use image. As yet another example, the transmission unit, after transmitting predetermined instruction information to the external equipment, may further transmit to the external equipment cancellation information giving an instruction to cancel the predetermined instruction information if a user performs an operation to cancel the predetermined cancellation information.

According to the present technology, as outlined above, the image data is received from the external equipment. The instruction information regarding the image data is generated. The instruction information is then transmitted to the external equipment. This enables the transmission of the instruction information regarding the image data to the external equipment A further concept of the present technology is to provide an image processing system including an image pickup apparatus and a picked-up image monitoring apparatus. The image pickup apparatus includes: an image pickup unit configured to obtain moving image data by imaging a subject; a transmission unit configured to transmit image data corresponding to the moving image data to the picked-up image monitoring apparatus; a reception unit configured to receive instruction information regarding the image data from the picked-up image monitoring apparatus; a display-use image generating unit configured to generate display-use image based on and reflecting the instruction information; and a display unit configured to display the display-use image. The picked-up image monitoring apparatus includes: a reception unit configured to receive the image data from the image pickup apparatus; a display unit configured to display an image derived from the image data; a processing unit configured to generate instruction information regarding the image data; and a transmission unit configured to transmit the instruction information to the image pickup apparatus.

Advantageous Effect of Invention

According to the present technology, the display of instruction information regarding image data from external equipment is made possible. Incidentally, the advantageous effects stated in this description are only examples and are not limitative of the present technology. There may be additional advantageous effects derived from this description.

BRIEF DESCRIPTION OF DRAWINGS

FIG. 1 is a block diagram depicting an example of the configuration of an image pickup system as one embodiment of the present technology.

FIG. 2 is a view depicting an example of a correspondence table listing the correspondence between the operations performed by a user on a touch panel on the one hand and instruction types and display details on the other hand.

FIG. 3 is a view depicting an example of the configuration of a data packet.

DESCRIPTION OF EMBODIMENTS

Figure 4:
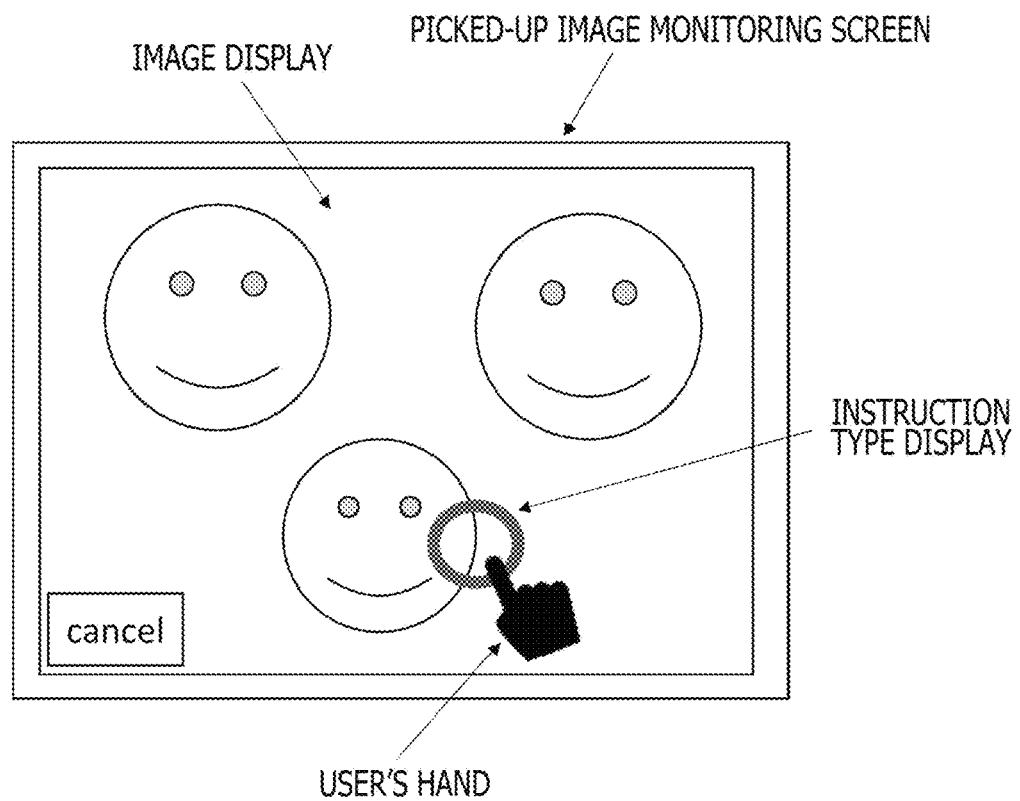
FIG. 4 is a view depicting an example of a display state in a case where the user of a picked-up image monitoring apparatus performs a "single tap" operation, i.e., an image pickup targeting instruction operation.

Preferred embodiments for implementing the present technology (referred to as the embodiments) are described below. The description will be given under the following headings:
  1. Embodiments
  2. Application Examples
  3. Alternative Examples 1. Embodiments Example of Configuration of Image Pickup System FIG. 1 depicts an example of the configuration of an image pickup system 10 as one embodiment of the present technology. The image pickup system 10 includes a video camera 100 and a picked-up image monitoring apparatus 200.

The video camera 100 obtains moving image data by imaging a subject. The video camera 100 further generates monitoring-use image data on the basis of the moving image data. The video camera 100 transmits the monitoring-use image data to the picked-up image monitoring apparatus 200 via a network such as any one of wireless networks including Wi-Fi or of wired networks. The monitoring-use image data is made smaller in size and lower in transmission bit rate than the original image data.

The picked-up image monitoring apparatus 200 is configured with terminal equipment such as a smartphone, a tablet, or a personal computer, for example. The picked-up image monitoring apparatus 200 receives the monitoring-use image data transmitted from the video camera 100 via the network. The picked-up image monitoring apparatus 200 then causes a display unit to display an image (picked-up image) derived from the monitoring-use image data. Incidentally, the picked-up image monitoring apparatus 200 need not necessarily be physically integrated with the display unit.

On the picked-up image monitoring apparatus 200, the user as the monitoring person (i.e., operator) may perform various image pickup instruction operations accompanied by position designation on the image displayed on the display unit. For example, the user performs such image pickup instruction operations using a touch panel provided on the display unit or a pointing device such as a mouse.

FIG. 2 depicts an example of a correspondence table listing the correspondence between the operations performed by the user on the touch panel on the one hand and instruction types and display details on the other hand. For example, the picked-up image monitoring apparatus 200 is provided with multiple default correspondence tables. The picked-up image monitoring apparatus 200 is enabled to select one of the multiple default correspondence tables for actual use. The picked-up image monitoring apparatus 200 is further enabled either to modify the selected default correspondence table as needed for actual use or to create a new correspondence table.

Although the example in the illustration indicates the correspondence table assumed to be used for operations on the touch panel, a correspondence table may similarly be configured for operations involving the use of a pointing device such as a mouse. In the illustrated example, the items of color, shape, and movement constitute display information representing display details (marks) displayed on the screen to indicate the instruction types. Also in the illustrated example, the item of instruction type constitutes display information representing display details (texts) displayed on the screen to indicate the instruction types.

In a case where, as will be discussed later, the user performs an image pickup instruction operation on the picked-up image monitoring apparatus 200, both the picked-up image monitoring apparatus 200 and the video camera 100 displays the instruction type on the screen displaying the picked-up image. In this case, three types of display details are conceivable: a mark only, a text only, and both a mark and a text. Both the picked-up image monitoring apparatus 200 and the video camera 100 are enabled to set one of the types of display details as the type of display.

The picked-up image monitoring apparatus 200 transmits beforehand information regarding the correspondence table to be actually used to the video camera 100. This allows the picked-up image monitoring apparatus 200 and the video camera 100 to share the correspondence table information therebetween.

What follows is an explanation of the illustrated example. Identification information ID="1" is associated with the operation "single tap," the instruction type "point," the color "blue," the shape "circle," and the movement "fixed." Identification information ID="2" is associated with the operation "double tap," the instruction type "zoom out," the color "orange," the shape "circle," and the movement "from inside to outside."

Identification information ID="3" is associated with the operation "long tap," the instruction type "zoom in," the color "blue," the shape "rectangle," and the movement "from outside to inside." Identification information ID="4" is associated with the operation "flick," the instruction type "fast pan," the color "light blue," the shape "arrow," and the movement "fixed." Identification information ID="5" is associated with the operation "swipe," the instruction type "slow pan," the color "yellowish green," the shape "arrow," and the movement "fixed."

In a case where the user performs an image pickup instruction operation on the touch panel, the picked-up image monitoring apparatus 200 displays, using a mark for example, the instruction type in a manner corresponding to the operation position on the image displayed on the display unit. This allows the user (operator) of the picked-up image monitoring apparatus 200 to verify the image pickup instruction operation that the user has carried out.

Also in this case, the picked-up image monitoring apparatus 200 transmits to the video camera 100 a data packet including position information and display information (ID) as image pickup instruction information. On the basis of the position information and the display information, the video camera 100 displays, using a mark for example, the details corresponding to the display information, i.e., the instruction type in the position corresponding to the position information associated with the image displayed on the display unit (finder). This allows the camera operator of the video camera 100 to recognize that the image pickup instruction of the displayed instruction type has been issued and to carry out accordingly an image pickup operation in line with the image pickup instruction.

FIG. 3 depicts an example of the configuration of a data packet. A field (a) holds identification information identifying this data packet including the image pickup instruction information. A field (b) holds ID (see FIG. 2) identifying the instruction type. A field (c) holds the x coordinate of the operation position. A field (d) holds the y coordinate of the operation position. A field (e) holds the x coordinate of the ending point of a displayed arrow originating from the operation position as the starting point. A field (f) holds the y coordinate of the ending point. The origin of the coordinates (0, 0) is at the top left corner, for example.

The display unit of the picked-up image monitoring apparatus 200 also displays a cancel button. The user (operator) of the picked-up image monitoring apparatus 200 may cancel the most-recently performed image pickup instruction operation by operating the cancel button. The picked-up image monitoring apparatus 200 need not be configured to have the cancel button displayed on the image. Alternatively, the picked-up image monitoring apparatus 200 may be equipped with a mechanical cancel button.

In a case where the user (operator) of the picked-up image monitoring apparatus 200 operates the cancel button, the picked-up image monitoring apparatus 200 indicates cancellation of the most-recently issued image pickup instruction by displaying, for example, characters such as "cancel" on the image, not depicted. In this case, the picked-up image monitoring apparatus 200 transmits cancellation information to the video camera 100. On the basis of the cancellation information, the video camera 100 indicates cancellation of the most-recently issued image pickup instruction by displaying, for example, characters such as "cancel" on the image. This allows the camera operator of the video camera 100 to recognize cancellation of the most-recently issued image pickup instruction.

Explained below as an example is a case where the user performs the "single tap" operation on the touch panel. The picked-up image monitoring apparatus 200 determines that the user has issued a "point" instruction, i.e., an image pickup targeting instruction. In this case, the picked-up image monitoring apparatus 200 displays the image pickup targeting instruction corresponding to the tapped position on the image displayed on the display unit. In this case, for example, a blue, fixed circular mark is displayed for a predetermined time period. Alternatively, a text "point" is displayed for a predetermined time period singly or in combination with the mark.

FIG. 4 depicts an exemplary display state in a case where the user performs a "single tap" operation, i.e., an image pickup targeting instruction operation, on the image displayed on the display unit of the picked-up image monitoring apparatus 200. In this case, a mark indicative of the image pickup targeting instruction is displayed corresponding to the position where the user has performed the "single tap" operation on the image. This allows the user (operator) of the picked-up image monitoring apparatus 200 to verify the image pickup targeting instruction operation that the user has carried out.

Also in this case, the picked-up image monitoring apparatus 200 transmits to the video camera 100 a data packet holding the display information "ID="1"" accompanied by position information regarding the tapped position as the image pickup instruction information. On the basis of the position information and the display information, the video camera 100 displays on the image a mark indicative of the image pickup targeting instruction corresponding to the position where the user of the picked-up image monitoring apparatus 200 has performed the "single tap" operation.

Figure 5:
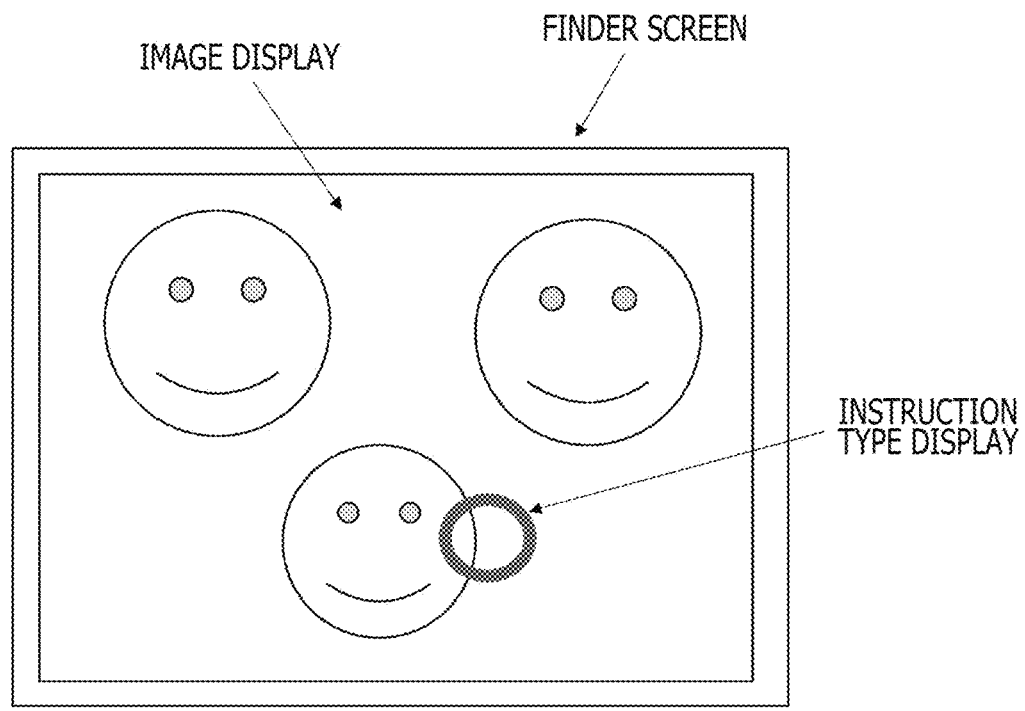
FIG. 5 is a view depicting an example of the display state on a display unit of a video camera in a case where the user of the picked-up image monitoring apparatus performs the "single tap" operation, i.e., the image pickup targeting instruction operation.
Figure 6:
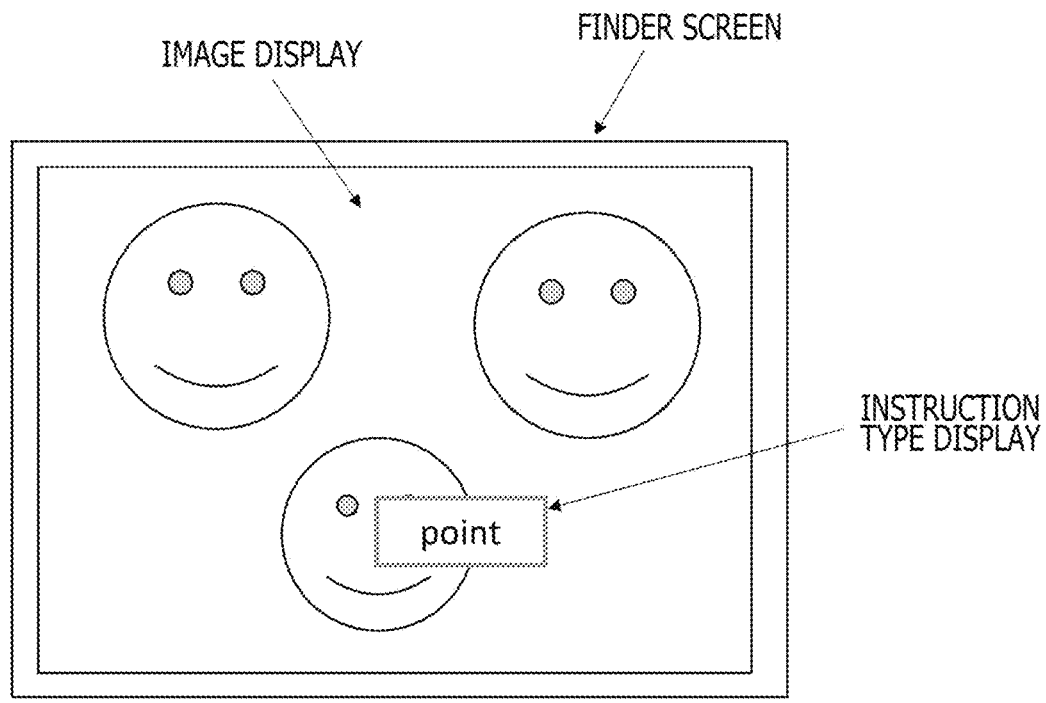
FIG. 6 is a view depicting another example of the display state on the display unit of the video camera in a case where the user of the picked-up image monitoring apparatus performs the "single tap" operation, i.e., the image pickup targeting instruction operation.

FIG. 5 depicts an example of the display state on the display unit of the video camera 100 in the above case. This allows the camera operator of the video camera 100 to recognize that the image corresponding to the mark display position is the image pickup target. Accordingly, the camera operator performs an image pickup operation such that the image pickup target is at the center of the picked-up image, for example. Note that an example in FIG. 6 indicates that the instruction type is displayed using the text "point." Conceivably, the instruction type may also be displayed using both a mark and a text, not illustrated.

Explained below as another example is a case in which the user performs a "double tap" operation on the touch panel. The picked-up image monitoring apparatus 200 determines that the user has issued a "zoom out" instruction. In this case, the picked-up image monitoring apparatus 200 displays the zoom-out instruction being issued corresponding to the tapped position on the image displayed on the display unit. In the present case, for example, an orange circular mark expanding repeatedly from inside to outside is displayed for a predetermined time period. Alternatively, a text "zoom out" is displayed for a predetermined time period singly or in combination with the mark. This allows the user (operator) of the picked-up image monitoring apparatus 200 to verify the zoom-out instruction operation that the user has carried out.

Also in this case, the picked-up image monitoring apparatus 200 transmits to the video camera 100 a data packet holding the display information "ID="2"" accompanied by position information regarding the tapped position as the image pickup instruction information. On the basis of the position information and the display information, the video camera 100 displays on the image a mark and/or a text indicative of the zoom-out instruction in a manner corresponding to the position where the user of the picked-up image monitoring apparatus 200 has performed the "double tap" operation.

Figure 7:
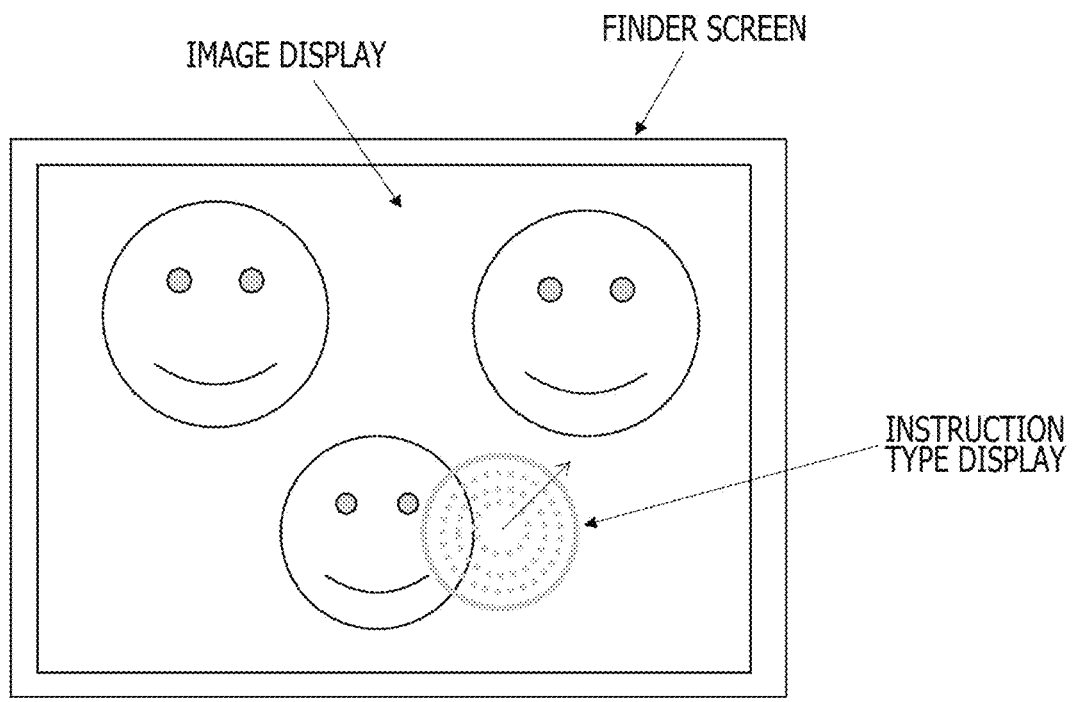
FIG. 7 is a view depicting an example of the display state on the display unit of the video camera in a case where the user of the picked-up image monitoring apparatus performs a "double tap" operation, i.e., a zoom-out instruction operation.
Figure 8:
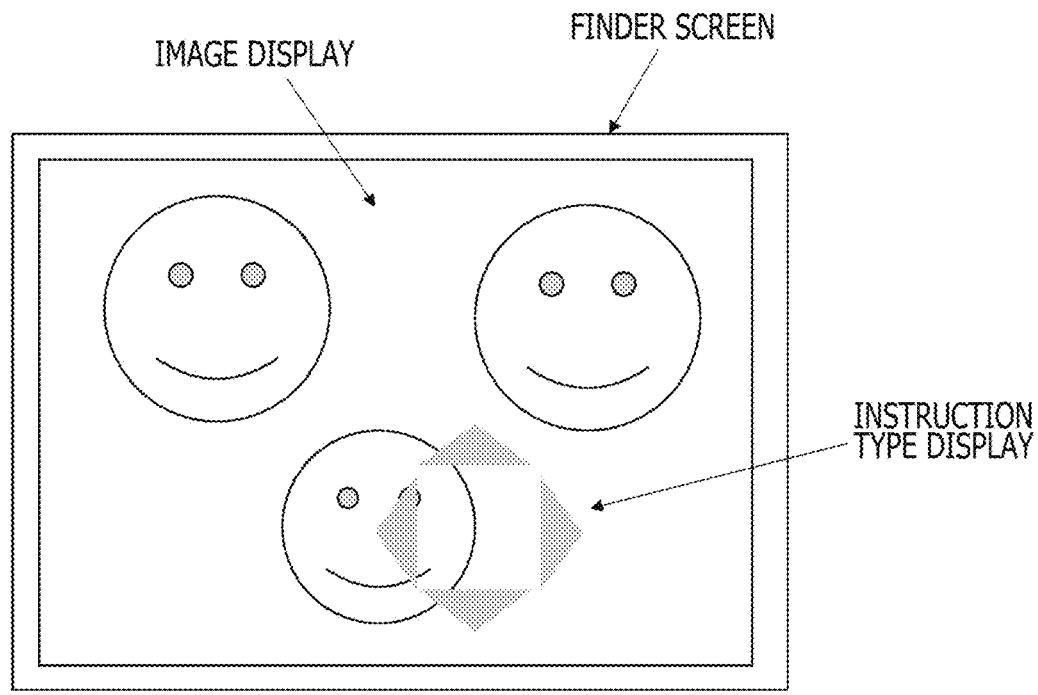
FIG. 8 is a view depicting another example of the display state on the display unit of the video camera in a case where the user of the picked-up image monitoring apparatus performs the "double tap" operation, i.e., the zoom-out instruction operation.

FIG. 7 depicts an example of the display state on the display unit of the video camera 100 in the above case. In this example, the display unit displays a mark indicative of the zoom-out instruction, i.e., an orange circular mark expanding repeatedly from inside to outside in a manner corresponding to the position where the user of the picked-up image monitoring apparatus 200 has performed the "double tap" operation. This allows the camera operator of the video camera 100 to recognize the zoom-out instruction for a zoom-out centering on the image corresponding to the mark display position. Accordingly, the camera operator performs a zoom-out operation centering on the image corresponding to the mark display position. FIG. 8 depicts an example of a fixed mark indicative of the zoom-out instruction.

Furthermore, explained below as another example is a case in which the user performs a "long tap" operation on the touch panel. The picked-up image monitoring apparatus 200 determines that the user has issued a "zoom in" instruction. In this case, the picked-up image monitoring apparatus 200 displays the zoom-in instruction being issued corresponding to the tapped position on the image displayed on the display unit. In the present case, for example, a blue rectangular mark contracting repeatedly from outside to inside is displayed for a predetermined time period. Alternatively, a text "zoom in" is displayed for a predetermined time period singly or in combination with the mark. This allows the user (operator) of the picked-up image monitoring apparatus 200 to verify the zoom-in instruction operation that the user has carried out.

Also in this case, the picked-up image monitoring apparatus 200 transmits to the video camera 100 a data packet holding the display information "ID="3"" accompanied by position information regarding the tapped position as the image pickup instruction information. On the basis of the position information and the display information, the video camera 100 displays on the image a mark and/or a text indicative of the zoom-in instruction in a manner corresponding to the position where the user of the picked-up image monitoring apparatus 200 has performed the "long tap" operation.

Figure 9:
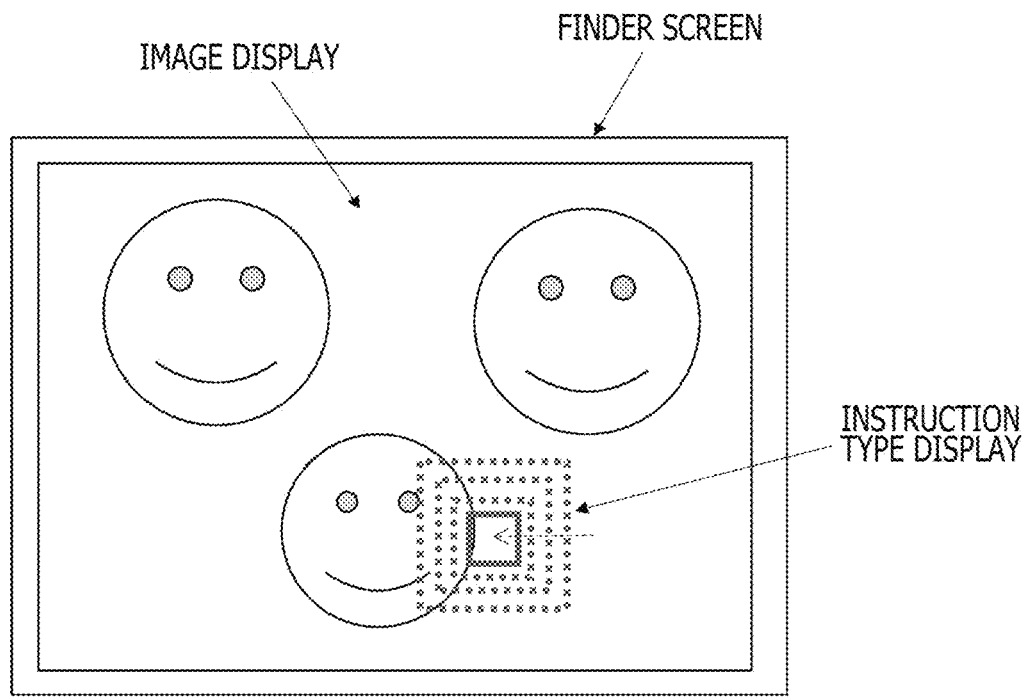
FIG. 9 is a view depicting an example of the display state on the display unit of the video camera in a case where the user of the picked-up image monitoring apparatus performs a "long tap" operation, i.e., a zoom-in instruction operation.
Figure 10:
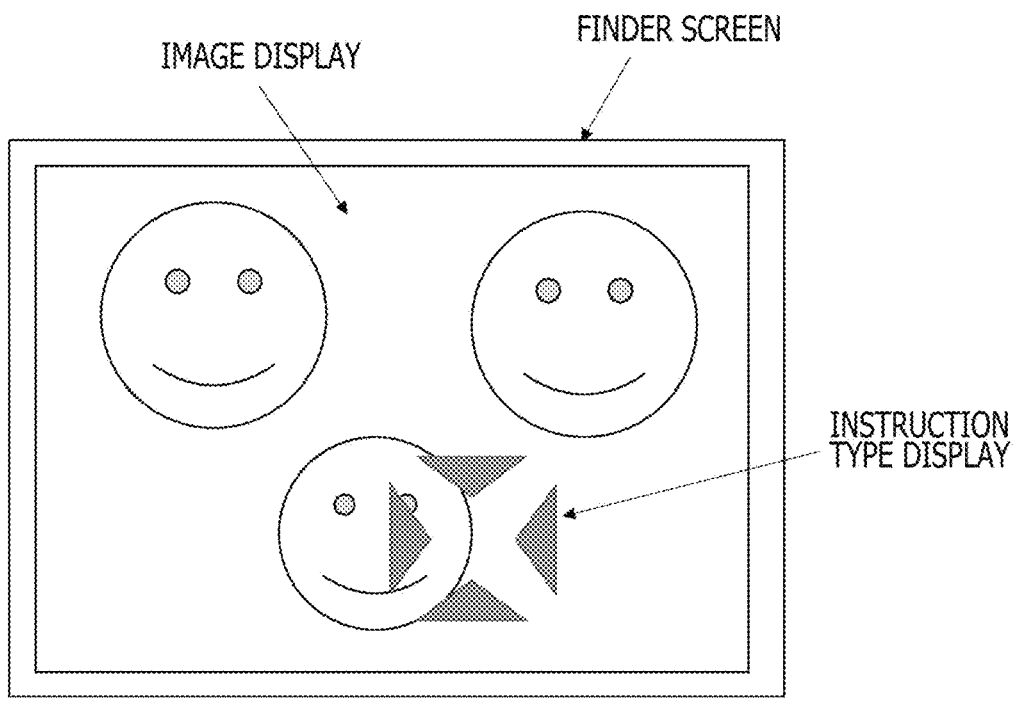
FIG. 10 is a view depicting another example of the display state on the display unit of the video camera in a case where the user of the picked-up image monitoring apparatus performs the "long tap" operation, i.e., the zoom-in instruction operation.

FIG. 9 depicts an example of the display state on the display unit of the video camera 100 in the above case. In this example, the display unit displays a mark indicative of the zoom-in instruction, i.e., a blue rectangular mark contracting repeatedly from outside to inside, in a manner corresponding to the position where the user of the picked-up image monitoring apparatus 200 has performed the "long tap" operation. This allows the camera operator of the video camera 100 to recognize the zoom-in instruction for a zoom-in centering on the image corresponding to the mark display position. Accordingly, the camera operator performs a zoom-in operation centering on the image corresponding to the mark display position. FIG. 10 depicts an example of a fixed mark indicative of the zoom-in instruction.

Explained below as a further example is a case in which the user performs a "flick" operation on the touch panel. The picked-up image monitoring apparatus 200 determines that the user has issued a "fast pan" instruction. In this case, the picked-up image monitoring apparatus 200 displays the fast-pan instruction being issued corresponding to the flicked position on the image displayed on the display unit.

In the present case, for example, a fixed light blue arrow mark is displayed for a predetermined time period. Alternatively, a text "fast pan" is displayed for a predetermined time period singly or in combination with the mark. For example, the fixed arrow mark originates from the starting point of the flick and is given a predetermined length in the flicked direction pointing to the pan direction. This allows the user (operator) of the picked-up image monitoring apparatus 200 to verify the fast-pan operation that the user has carried out.

Also in this case, the picked-up image monitoring apparatus 200 transmits to the video camera 100 a data packet holding the display information "ID="4"" accompanied by position information regarding the flicked position as the image pickup instruction information. On the basis of the position information and the display information, the video camera 100 displays on the image a mark and/or a text indicative of the fast-pan instruction in a manner corresponding to the position where the user of the picked-up image monitoring apparatus 200 has performed the "flick" operation.

Figure 11:
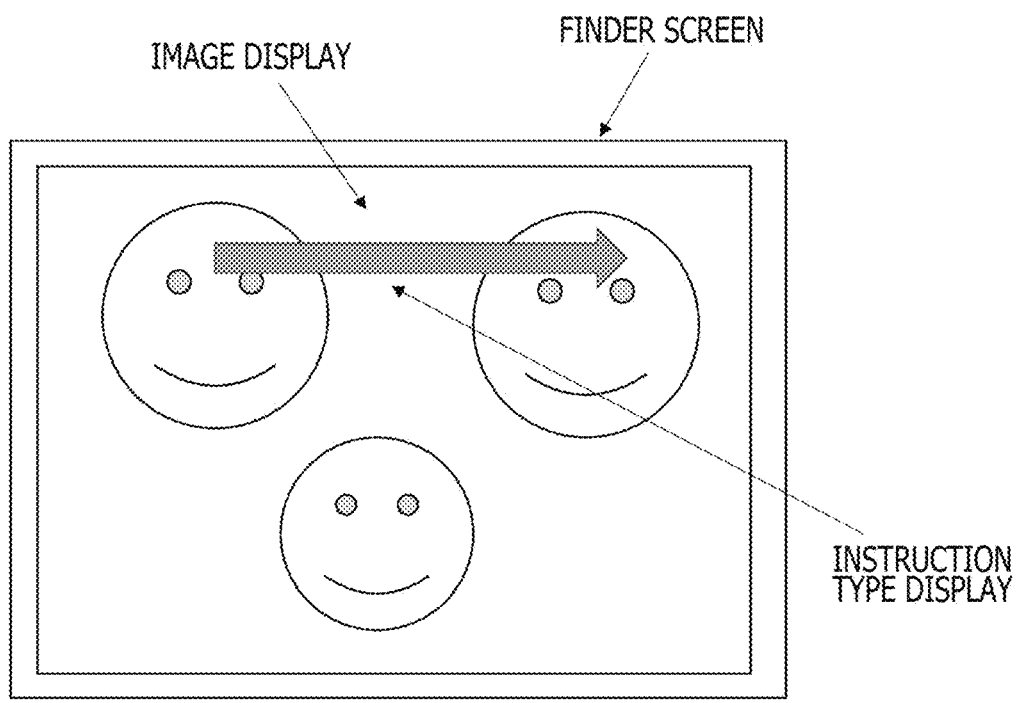
FIG. 11 is a view depicting an example of the display state on the display unit of the video camera in a case where the user of the picked-up image monitoring apparatus performs a "flick" operation, i.e., a fast-pan instruction operation.

FIG. 11 depicts an example of the display state on the display unit of the video camera 100 in the above case. In this example, the display unit displays a mark indicative of the fast-pan instruction as well as the pan direction, i.e., a fixed light blue arrow mark, in a manner corresponding to the position where the user of the picked-up image monitoring apparatus 200 has performed the "flick" operation. This allows the camera operator of the video camera 100 to recognize the fast-pan instruction for a fast-pan in the arrowed direction. Accordingly, the camera operator performs a fast-pan operation in that direction.

Explained below as another example is a case in which the user performs a "swipe" operation on the touch panel. The picked-up image monitoring apparatus 200 determines that the user has issued a "slow pan" instruction. In this case, the picked-up image monitoring apparatus 200 displays the slow-pan instruction being issued corresponding to the swiped position on the image displayed on the display unit.

In the present case, for example, a fixed yellowish green arrow mark is displayed for a predetermined time period. Alternatively, a text "slow pan" is displayed for a predetermined time period singly or in combination with the mark. For example, the fixed arrow mark originates from the starting point of the swipe and is given a predetermined length in the swiped direction pointing to the pan direction. This allows the user (operator) of the picked-up image monitoring apparatus 200 to verify the slow-pan operation that the user has carried out.

Also in this case, the picked-up image monitoring apparatus 200 transmits to the video camera 100 a data packet holding the display information "ID="5" accompanied by position information regarding the swiped position. On the basis of the position information and the display information, the video camera 100 displays on the image a mark and/or a text indicative of the slow-pan instruction in a manner corresponding to the position where the user of the picked-up image monitoring apparatus 200 has performed the "swipe" operation. This allows the camera operator of the video camera 100 to recognize the slow-pan instruction for a slow-pan in the arrowed direction. Accordingly, the camera operator performs a slow-pan operation in that direction.

Example of the Configuration of the Video Camera

Figure 12:
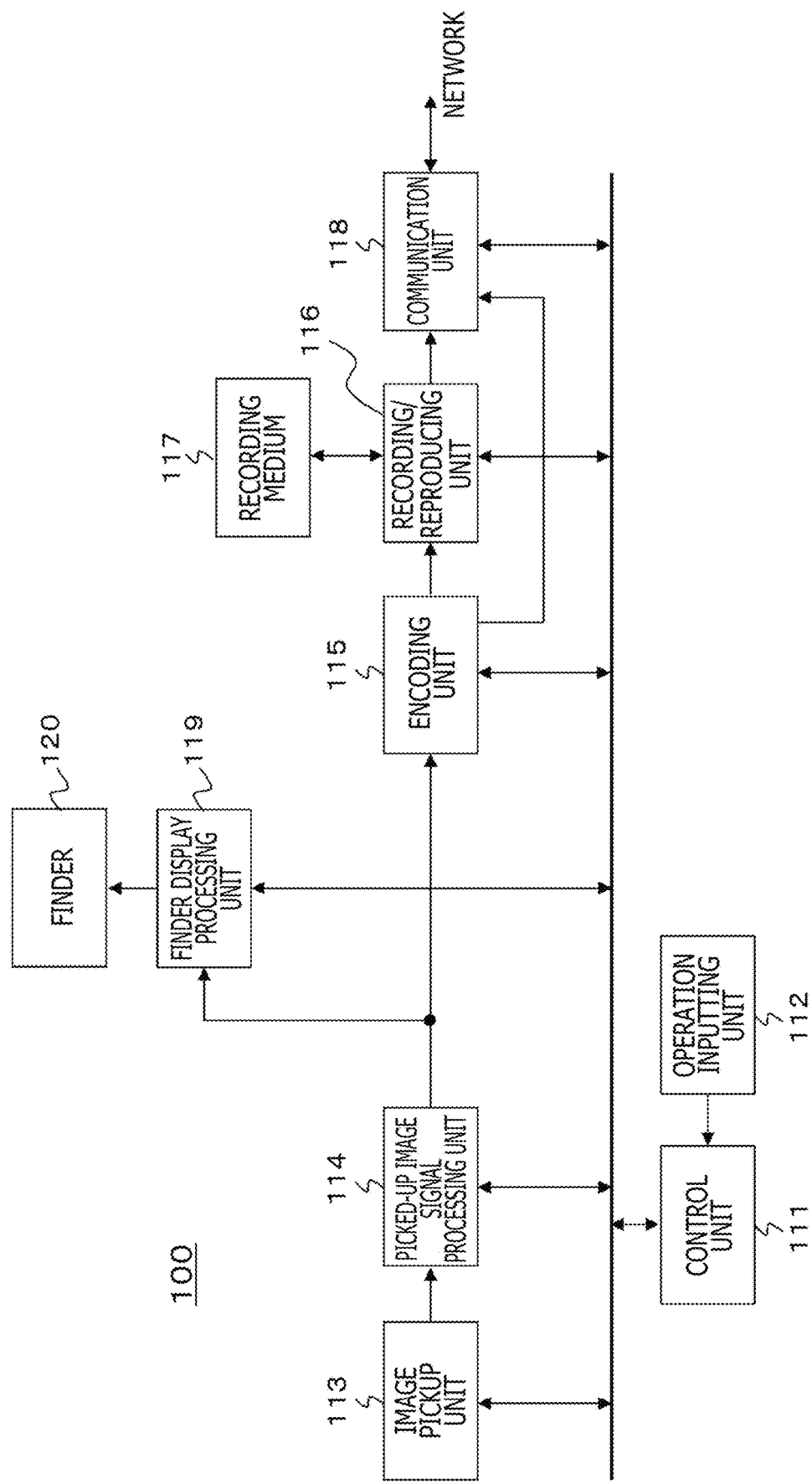
FIG. 12 is a block diagram depicting an example of the configuration of the video camera.

FIG. 12 depicts an example of the configuration of the video camera 100. The video camera 100 includes a control unit 111, an operation inputting unit 112, an image pickup unit 113, a picked-up image signal processing unit 114, an encoding unit 115, a recording/reproducing unit 116, a recording medium 117, a communication unit 118, a finder display processing unit 119, and a finder 120.

The control unit 111 controls the operations of the components in the video camera 100. The operation inputting unit 112 connected with the control unit 111 provides a user interface that accepts various operations performed by the user.

The image pickup unit 113 has an image pickup lens and an image pickup element (imager), not depicted. The image pickup unit 113 images a subject and outputs a picked-up image signal. The image pickup element may be a CCD (Charge-Coupled Device) image sensor or a CMOS (Complementary Metal-Oxide Semiconductor) image sensor, for example. The picked-up image signal processing unit 114 generates picked-up image data by performing such processes as sample hold, gain control, conversion from analog signal to digital signal, white balance adjustment, and gamma correction on the picked-up image signal (analog signal) output from the image pickup unit 113.

The encoding unit 115 generates encoded image data by performing data compression processing using the MPEG method, for example, on the picked-up image data generated by the picked-up image signal processing unit 114. On the basis of the picked-up image data, the encoding unit 115 further generates monitoring-use image data. The monitoring-use image data is made smaller in size and lower in transmission bit rate than the picked-up image data.

The recording/reproducing unit 116 records the encoded image data obtained by the encoding unit 115 to the recording medium 117. As needed, the recording/reproducing unit 116 reproduces the encoded image data from the recording medium 117. The recording medium 117 is configured with a memory card, for example. Here, a series of image data from the start to the end of recording is recorded as data of one clip. On the recording medium, the image data is filed in clips and managed by a file system.

The communication unit 118 communicates with the picked-up image monitoring apparatus 200 via any one of wireless networks including Wi-Fi or of wired networks. At the time of image pickup, the communication unit 118 sends to the picked-up image monitoring apparatus 200 the monitoring-use image data obtained by the encoding unit 115.

Also at the time of image pickup, when the user (operator) of the picked-up image monitoring apparatus 200 performs an image pickup instruction operation, the communication unit 118 receives a data packet (see FIG. 3) including position information and display information (ID) as image pickup instruction information from the picked-up image monitoring apparatus 200 via the network. The data packet is sent to the control unit 111. This enables the control unit 111 to recognize the position information and the display information (ID) as the image pickup instruction information.

Also, the communication unit 118 receives beforehand the information regarding the correspondence table (see FIG. 2) from the picked-up image monitoring apparatus 200 via the network, the correspondence table denoting the correspondence between the operations performed by the user on the touch panel on the one hand and instruction types and display details on the other hand, the table being used by the picked-up image monitoring apparatus 200 in operation. The correspondence table information is sent to the control unit 111 and held in a memory. This enables the control unit 111 to reference the correspondence table in preparing display data for displaying the image pickup instruction details (instruction type) corresponding to the display information (ID).

Also at the time of image pickup, when the user (operator) of the picked-up image monitoring apparatus 200 performs an operation to cancel the most-recently issued image pickup instruction, the communication unit 118 receives information for cancelling the image pickup instruction from the picked-up image monitoring apparatus 200 via the network. Furthermore, the communication unit 118 communicates with an editor terminal apparatus, not depicted, and transmits the clip data reproduced from the recording medium 117 to the editor terminal apparatus.

The finder display processing unit 119 generates finder-use image data on the basis of the picked-up image data generated by the picked-up image signal processing unit 114. In this case, the finder display processing unit 119 under control of the control unit 111 synthesizes and sends display data to the finder 120 serving as the display unit, the display data representing the image pickup instruction details (instruction type) corresponding to the display information (ID) supplied from the control unit 111, the display data being synthesized in such a manner that the image pickup instruction details are displayed in the position based on the position information.

In turn, the finder 120 displays, for example, a mark indicative of the instruction type in the position corresponding to the position information associated with the image. This allows the camera operator of the video camera 100 to recognize that an image pickup instruction of the instruction type has been issued and to perform an image pickup operation in line with that image pickup instruction.

Further, upon receipt of the information for cancelling the image pickup instruction from the picked-up image monitoring apparatus 200, the finder display processing unit 119 inserts display data for displaying the cancellation into the finder-use image data. In this case, an overlay display of the image pickup instruction cancellation appears on the image displayed on the finder 120. This prompts the camera operator of the video camera 100 to immediately recognize the image pickup instruction being cancelled and to avoid carrying out the image pickup operation in line with the image pickup instruction.

Example of the Configuration of the Picked-Up Image Monitoring Apparatus

Figure 13:
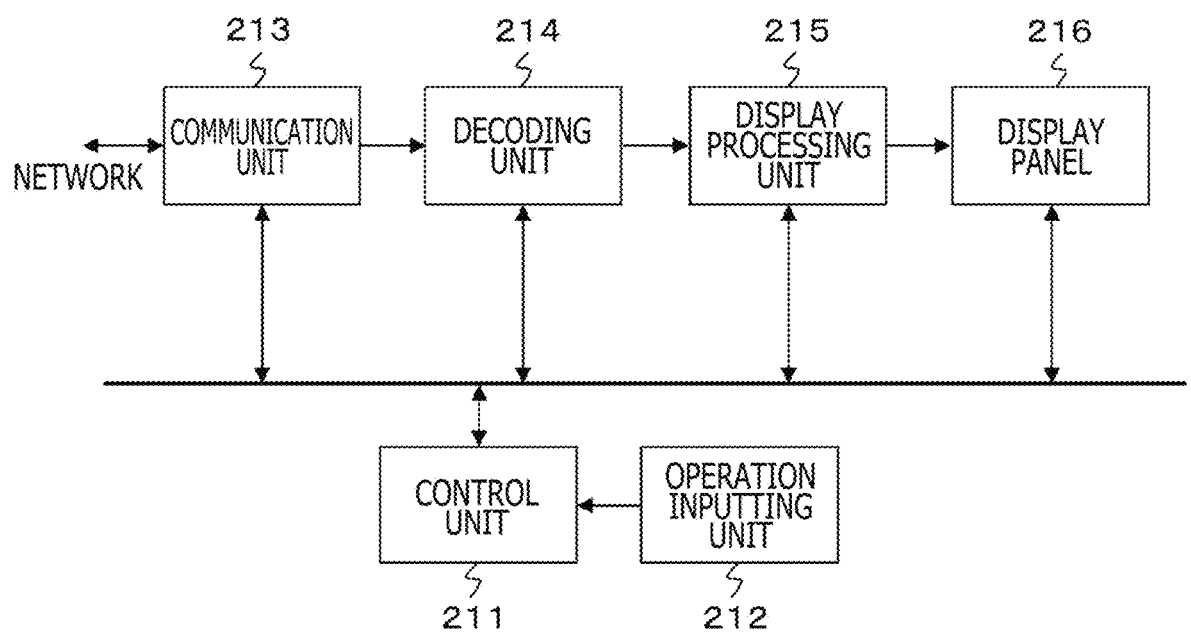
FIG. 13 is a block diagram depicting an example of the configuration of the picked-up image monitoring apparatus.

FIG. 13 depicts an example of the configuration of the picked-up image monitoring apparatus 200. The picked-up image monitoring apparatus 200 includes a control unit 211, an operation inputting unit 212, a communication unit 213, a decoding unit 214, a display processing unit 215, and a display panel 216.

The control unit 211 controls the operations of the components in the picked-up image monitoring apparatus 200. The operation inputting unit 212 connected with the control unit 211 provides a user interface that accepts various operations performed by the user. The operation inputting unit 212 is configured, for example, with mechanical operation buttons or a touch panel mounted on a screen of the display panel 216.

The user may carry out image pickup instruction operations using the touch panel mounted on the screen of the display panel 216. The control unit 211 recognizes the instruction type of the operation performed by the user on the touch panel and the display details to which the operation corresponds on the basis of the correspondence table (see FIG. 2) held in a memory of the control unit 211. The user may operate the operation inputting unit 212 to set beforehand the correspondence table to be actually used by the picked-up image monitoring apparatus 200.

The communication unit 213 communicates with the video camera 100 via any one of wireless networks including Wi-Fi or of wired networks. At the time of image pickup with the video camera 100, the communication unit 213 receives the monitoring-use image data from the video camera 100 via the network.

Also at the time of image pickup with the video camera 100, when the user (camera operator) performs an image pickup instruction operation, the communication unit 213 transmits a data packet (see FIG. 3) including position information and display information (ID) as image pickup instruction information to the video camera 100 via the network. The data packet is supplied from the control unit 211 to the communication unit 213.

Also at the time of image pickup with the video camera 100, when the user (camera operator) performs an operation to cancel the most-recently issued image pickup instruction, the communication unit 213 transmits information for cancelling the image pickup instruction to the video camera 100 via the network.

Further, before image pickup with the video camera 100, the communication unit 213 transmits the information regarding the correspondence table to be actually used by the picked-up image monitoring apparatus 200 to the video camera 100 via the network so that the two apparatuses may share the information therebetween. The correspondence table information is supplied from the control unit 211 to the communication unit 213.

The decoding unit 214 decodes the monitoring-use image data (encoded image data) received by the communication unit 213. The display processing unit 215 generates image data for display panel use on the basis of the monitoring-use image data obtained by the decoding unit 214.

In the above case, when the user (camera operator) performs an image pickup instruction operation, the display processing unit 215 under control of the control unit 211 synthesizes and sends display data to the display panel 216 serving as the display unit, the display data representing the image pickup instruction details (instruction type) corresponding to the display information (ID) supplied from the control unit 211, the display data being synthesized in such a manner that the image pickup instruction details are displayed in the position based on the position information.

As discussed above, the video camera 100 in the image pickup system 10 in FIG. 1 transmits the monitoring-use image data corresponding to the picked-up image data to the picked-up image monitoring apparatus 200. The video camera 100 receives display information accompanied by position information from the picked-up image monitoring apparatus 200. The video camera 100 then provides finder display data in such a manner that the image data corresponding to moving image data is overlaid with the display data indicative of the image pickup instruction details (instruction type) corresponding to the display information, the image pickup instruction details being displayed in the position based on the position information. This makes it possible to display the image pickup instruction details set by the picked-up image monitoring apparatus 200 in a manner associated with the position designated by the picked-up image monitoring apparatus 200 on the picked-up image.

Further, the picked-up image monitoring apparatus 200 in the image pickup system 10 in FIG. 1 receives from the video camera 100 the monitoring-use image data corresponding to the picked-up image data. In turn, the picked-up image monitoring apparatus 200 generates display information accompanied by position information based on the user's operations including designation of the position on the display image derived from the monitoring-use image data. The picked-up image monitoring apparatus 200 transmits the display information thus generated to the video camera 100. This enables the video camera 100 to display the image pickup instruction details set in association with the position designated on the picked-up image.

Furthermore, the image pickup system 10 in FIG. 1 permits accurate issuing of the image pickup targeting instruction and other image pickup instructions from a remote location connected via the network. For example, it is possible to issue precise image pickup instructions from a TV station to a remotely-located camera operator. Because the image pickup target is designated without recourse to voice information, the system can be utilized extensively in situations where the use of voice is ruled out, such as on golf courses, on tennis courts, or in concert halls.

Moreover, the utilization of instruction marks or texts makes it possible to issue instructions intuitively without using language. Having the instructions displayed on the finder contributes to training novice camera operators. Also, because the image pickup system 10 alone completes the cycle of issuing image pickup instructions and carrying out image pickup operations, those in the field are little affected by potential troubles of audio equipment.

2. Application Examples

The technology according to the present disclosure may be applied to diverse products. For example, the technology may be applied to a surgery room system.

Figure 14:
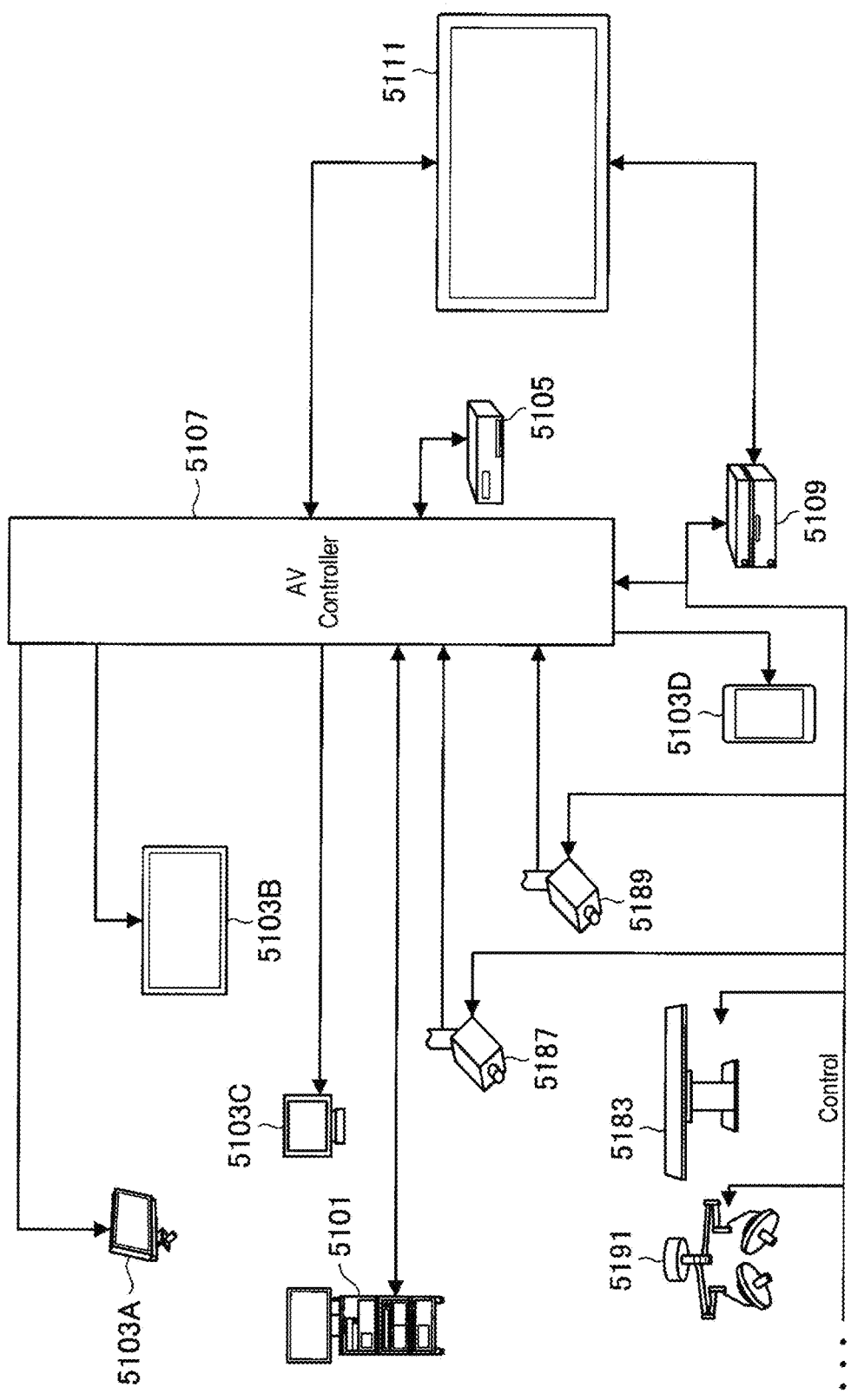
FIG. 14 is a view schematically depicting a general configuration of a surgery room system.

FIG. 14 is a view schematically depicting a general configuration of a surgery room system 5100 to which the technology according to an embodiment of the present disclosure can be applied. Referring to FIG. 14, the surgery room system 5100 is configured such that a group of apparatus installed in a surgery room are connected for cooperation with each other through an audiovisual (AV) controller 5107 and a surgery room controlling apparatus 5109.

In the surgery room, various apparatus may be installed. In FIG. 14, as an example, various apparatus group 5101 for endoscopic surgery, a ceiling camera 5187, a surgery field camera 5189, a plurality of display apparatus 5103A to 5103D, a recorder 5105, a patient bed 5183 and an illumination 5191 are depicted. The ceiling camera 5187 is provided on the ceiling of a surgery room and images the hands of a surgeon. The surgery field camera 5189 is provided on the ceiling of the surgery room and images a state of the entire surgery room.

Among the apparatus mentioned, the apparatus group 5101 belongs to an endoscopic surgery system 5113 hereinafter described and include an endoscope, a display apparatus which displays an image picked up by the endoscope and so forth. Various apparatus belonging to the endoscopic surgery system 5113 are referred to also as medical equipment. Meanwhile, the display apparatus 5103A to 5103D, the recorder 5105, the patient bed 5183 and the illumination 5191 are apparatus which are equipped, for example, in the surgery room separately from the endoscopic surgery system 5113. The apparatus which do not belong to the endoscopic surgery system 5113 are referred to also as non-medical equipment. The audiovisual controller 5107 and/or the surgery room controlling apparatus 5109 cooperatively control operation of the medical equipment and the non-medical equipment with each other.

The audiovisual controller 5107 integrally controls processes of the medical equipment and the non-medical equipment relating to image display. Specifically, each of the apparatus group 5101, the ceiling camera 5187 and the surgery field camera 5189 from among the apparatus provided in the surgery room system 5100 may be an apparatus having a function of sending information to be displayed during surgery (such information is hereinafter referred to as display information, and the apparatus mentioned is hereinafter referred to as apparatus of a sending source). Meanwhile, each of the display apparatus 5103A to 5103D may be an apparatus to which display information is outputted (the apparatus is hereinafter referred to also as apparatus of an output destination). Further, the recorder 5105 may be an apparatus which serves as both of an apparatus of a sending source and an apparatus of an output destination. The audiovisual controller 5107 has a function of controlling operation of an apparatus of a sending source and an apparatus of an output destination to acquire display information from the apparatus of a sending source and transmit the display information to the apparatus of an output destination so as to be displayed or recorded. It is to be noted that the display information includes various images picked up during surgery, various kinds of information relating to the surgery (for example, physical information of a patient, inspection results in the past or information regarding a surgical procedure) and so forth.

Specifically, to the audiovisual controller 5107, information relating to an image of a surgical region in a body lumen of a patient imaged by the endoscope may be transmitted as the display information from the apparatus group 5101. Further, from the ceiling camera 5187, information relating to an image of the hands of the surgeon picked up by the ceiling camera 5187 may be transmitted as display information. Further, from the surgery field camera 5189, information relating to an image picked up by the surgery field camera 5189 and illustrating a state of the entire surgery room may be transmitted as display information. It is to be noted that, if a different apparatus having an image pickup function exists in the surgery room system 5100, then the audiovisual controller 5107 may acquire information relating to an image picked up by the different apparatus as display information also from the different apparatus.

Alternatively, for example, in the recorder 5105, information relating to such images as mentioned above picked up in the past is recorded by the audiovisual controller 5107. The audiovisual controller 5107 can acquire, as display information, information relating to the images picked up in the past from the recorder 5105. It is to be noted that also various pieces of information relating to surgery may be recorded in advance in the recorder 5105.

The audiovisual controller 5107 controls at least one of the display apparatus 5103A to 5103D, which are apparatus of an output destination, to display acquired display information (namely, images picked up during surgery or various pieces of information relating to the surgery). In the example depicted, the display apparatus 5103A is a display apparatus installed so as to be suspended from the ceiling of the surgery room; the display apparatus 5103B is a display apparatus installed on a wall face of the surgery room; the display apparatus 5103C is a display apparatus installed on a desk in the surgery room; and the display apparatus 5103D is a mobile apparatus (for example, a tablet personal computer (PC)) having a display function.

Further, though not depicted in FIG. 14, the surgery room system 5100 may include an apparatus outside the surgery room. The apparatus outside the surgery room may be, for example, a server connected to a network constructed inside and outside the hospital, a PC used by medical staff, a projector installed in a meeting room of the hospital or the like. Where such an external apparatus is located outside the hospital, also it is possible for the audiovisual controller 5107 to cause display information to be displayed on a display apparatus of a different hospital through a teleconferencing system or the like to perform telemedicine.

The surgery room controlling apparatus 5109 integrally controls processes other than processes relating to image display on the non-medical equipment. For example, the surgery room controlling apparatus 5109 controls driving of the patient bed 5183, the ceiling camera 5187, the surgery field camera 5189 and the illumination 5191.

In the surgery room system 5100, a centralized operation panel 5111 is provided such that it is possible to issue an instruction regarding image display to the audiovisual controller 5107 or issue an instruction regarding operation of the non-medical equipment to the surgery room controlling apparatus 5109 through the centralized operation panel 5111. The centralized operation panel 5111 is configured by providing a touch panel on a display face of a display apparatus.

Figure 15:
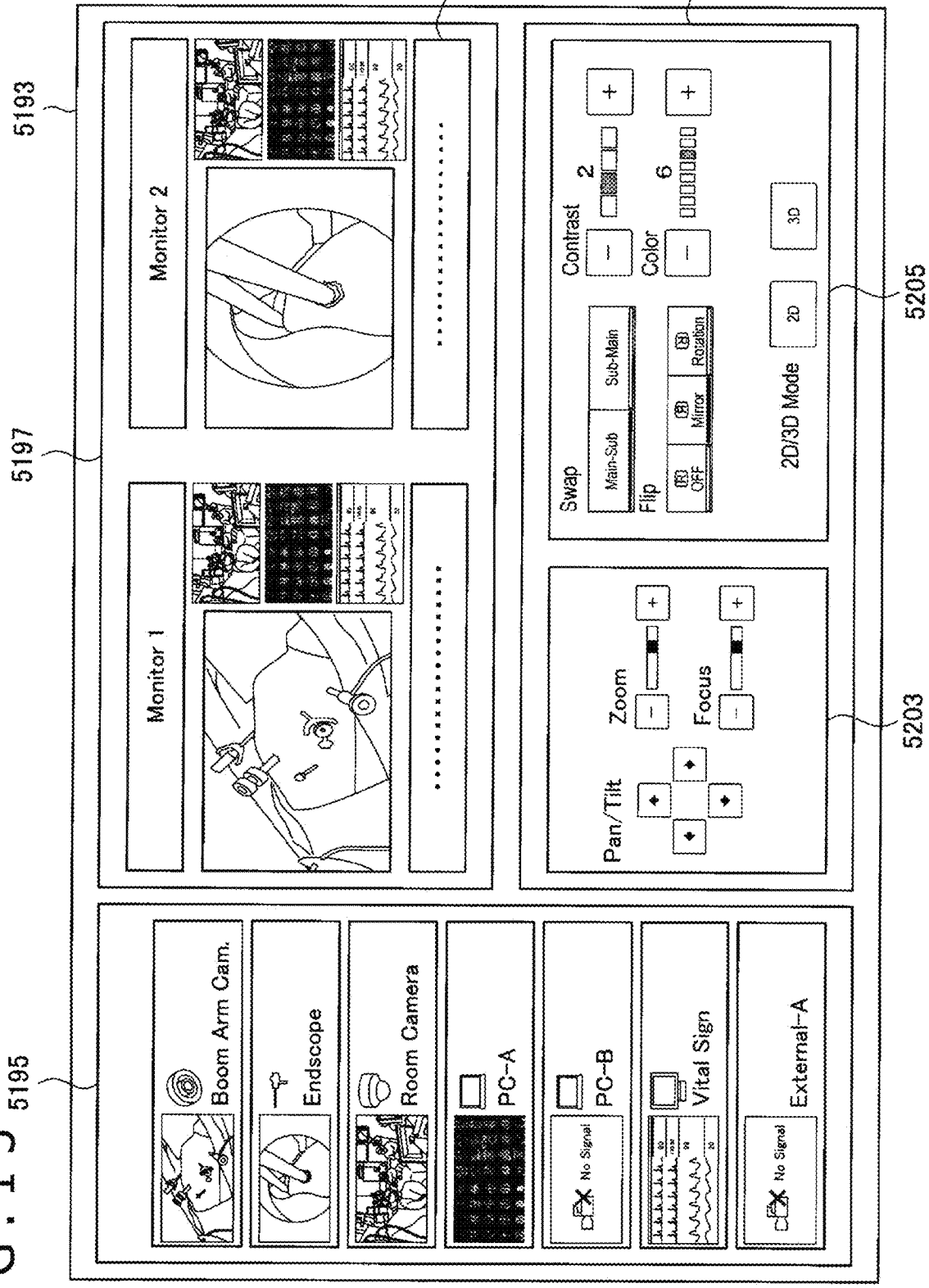
FIG. 15 is a view depicting an example of display of an operation screen image of a centralized operation panel.

FIG. 15 is a view depicting an example of display of an operation screen image on the centralized operation panel 5111. In FIG. 15, as an example, an operation screen image is depicted which corresponds to a case in which two display apparatus are provided as apparatus of an output destination in the surgery room system 5100. Referring to FIG. 15, the operation screen image 5193 includes a sending source selection region 5195, a preview region 5197 and a control region 5201.

In the sending source selection region 5195, the sending source apparatus provided in the surgery room system 5100 and thumbnail screen images representative of display information the sending source apparatus have are displayed in an associated manner with each other. A user can select display information to be displayed on the display apparatus from any of the sending source apparatus displayed in the sending source selection region 5195.

In the preview region 5197, a preview of screen images displayed on two display apparatus (Monitor 1 and Monitor 2) which are apparatus of an output destination is displayed. In the example depicted, four images are displayed by picture in picture (PinP) display in regard to one display apparatus. The four images correspond to display information sent from the sending source apparatus selected in the sending source selection region 5195. One of the four images is displayed in a comparatively large size as a main image while the remaining three images are displayed in a comparatively small size as sub images. The user can exchange between the main image and the sub images by suitably selecting one of the images from among the four images displayed in the region. Further, a status displaying region 5199 is provided below the region in which the four images are displayed, and a status relating to surgery (for example, elapsed time of the surgery, physical information of the patient and so forth) may be displayed suitably in the status displaying region 5199.

A sending source operation region 5203 and an output destination operation region 5205 are provided in the control region 5201. In the sending source operation region 5203, a graphical user interface (GUI) part for performing an operation for an apparatus of a sending source is displayed. In the output destination operation region 5205, a GUI part for performing an operation for an apparatus of an output destination is displayed. In the example depicted, GUI parts for performing various operations for a camera (panning, tilting and zooming) in an apparatus of a sending source having an image pickup function are provided in the sending source operation region 5203. The user can control operation of the camera of an apparatus of a sending source by suitably selecting any of the GUI parts. It is to be noted that, though not depicted, where the apparatus of a sending source selected in the sending source selection region 5195 is a recorder (namely, where an image recorded in the recorder in the past is displayed in the preview region 5197), GUI parts for performing such operations as reproduction of the image, stopping of reproduction, rewinding, fast-feeding and so forth may be provided in the sending source operation region 5203.

Further, in the output destination operation region 5205, GUI parts for performing various operations for display on a display apparatus which is an apparatus of an output destination (swap, flip, color adjustment, contrast adjustment and switching between two dimensional (2D) display and three dimensional (3D) display) are provided. The user can operate the display of the display apparatus by suitably selecting any of the GUI parts.

It is to be noted that the operation screen image to be displayed on the centralized operation panel 5111 is not limited to the depicted example, and the user may be able to perform operation inputting to each apparatus which can be controlled by the audiovisual controller 5107 and the surgery room controlling apparatus 5109 provided in the surgery room system 5100 through the centralized operation panel 5111.

Figure 16:
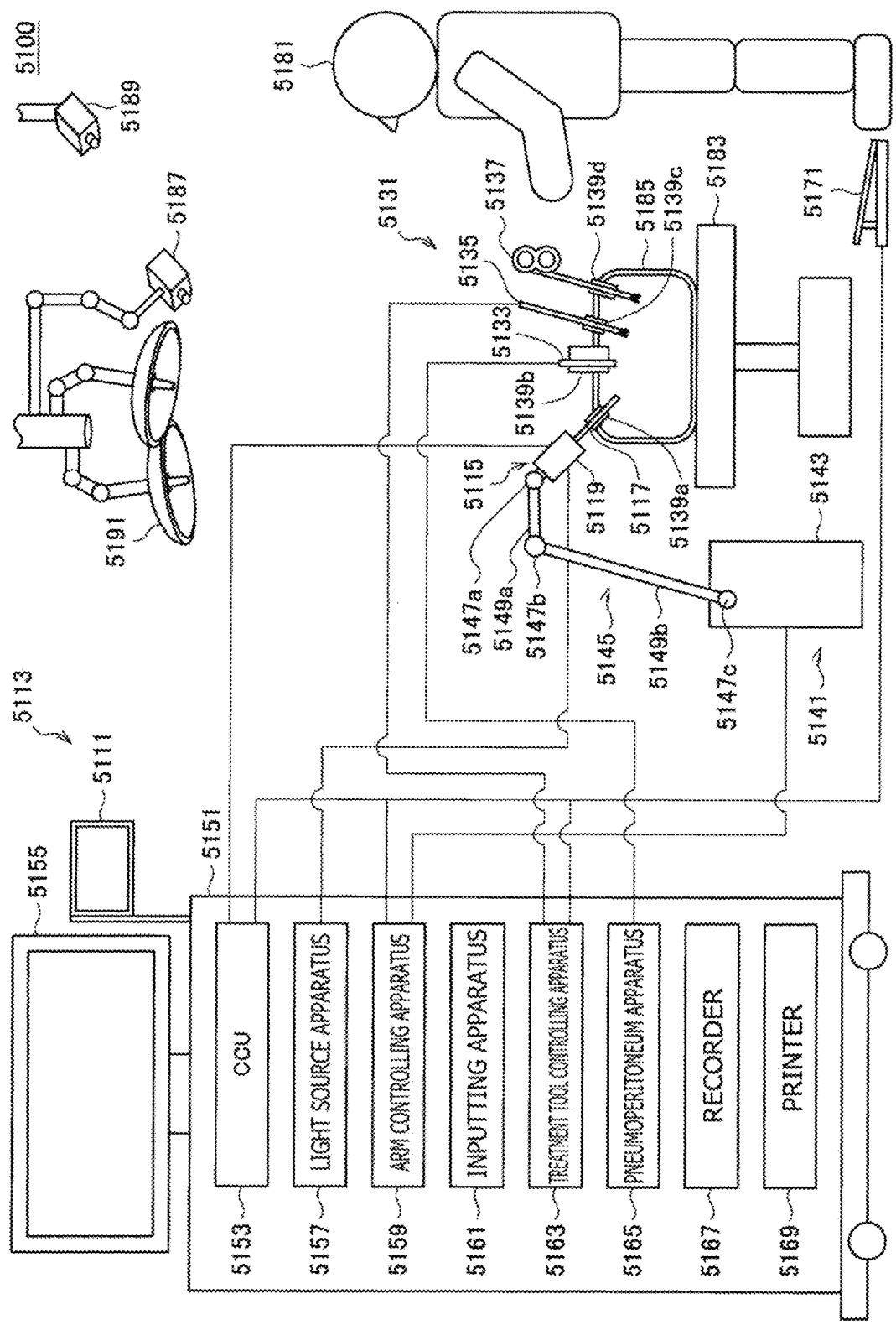
FIG. 16 is a view illustrating an example of a state of surgery to which the surgery room system is applied.

FIG. 16 is a view illustrating an example of a state of surgery to which the surgery room system described above is applied. The ceiling camera 5187 and the surgery field camera 5189 are provided on the ceiling of the surgery room such that it can image the hands of a surgeon (medical doctor) 5181 who performs treatment for an affected area of a patient 5185 on the patient bed 5183 and the entire surgery room. The ceiling camera 5187 and the surgery field camera 5189 may include a magnification adjustment function, a focal distance adjustment function, an imaging direction adjustment function and so forth. The illumination 5191 is provided on the ceiling of the surgery room and irradiates at least upon the hands of the surgeon 5181. The illumination 5191 may be configured such that the irradiation light amount, the wavelength (color) of the irradiation light, the irradiation direction of the light and so forth can be adjusted suitably.

The endoscopic surgery system 5113, the patient bed 5183, the ceiling camera 5187, the surgery field camera 5189 and the illumination 5191 are connected for cooperation with each other through the audiovisual controller 5107 and the surgery room controlling apparatus 5109 (not depicted in FIG. 16) as depicted in FIG. 14. The centralized operation panel 5111 is provided in the surgery room, and the user can suitably operate the apparatus existing in the surgery room through the centralized operation panel 5111 as described hereinabove.

In the following, a configuration of the endoscopic surgery system 5113 is described in detail. As depicted, the endoscopic surgery system 5113 includes an endoscope 5115, other surgical tools 5131, a supporting arm apparatus 5141 which supports the endoscope 5115 thereon, and a cart 5151 on which various apparatus for endoscopic surgery are mounted.

In endoscopic surgery, in place of incision of the abdominal wall to perform laparotomy, a plurality of tubular aperture devices called trocars 5139a to 5139d are used to puncture the abdominal wall. Then, a lens barrel 5117 of the endoscope 5115 and the other surgical tools 5131 are inserted into body lumens of the patient 5185 through the trocars 5139a to 5139d. In the example depicted, as the other surgical tools 5131, a pneumoperitoneum tube 5133, an energy treatment tool 5135 and forceps 5137 are inserted into body lumens of the patient 5185. Further, the energy treatment tool 5135 is a treatment tool for performing incision and peeling of a tissue, sealing of a blood vessel or the like by high frequency current or ultrasonic vibration. However, the surgical tools 5131 depicted are mere examples at all, and as the surgical tools 5131, various surgical tools which are generally used in endoscopic surgery such as, for example, a pair of tweezers or a retractor may be used.

An image of a surgical region in a body lumen of the patient 5185 picked up by the endoscope 5115 is displayed on a display apparatus 5155. The surgeon 5181 would use the energy treatment tool 5135 or the forceps 5137 while watching the image of the surgical region displayed on the display apparatus 5155 on the real time basis to perform such treatment as, for example, resection of an affected area. It is to be noted that, though not depicted, the pneumoperitoneum tube 5133, the energy treatment tool 5135, and the forceps 5137 are supported by the surgeon 5181, an assistant or the like during surgery.

(Supporting Arm Apparatus)

The supporting arm apparatus 5141 includes an arm unit 5145 extending from a base unit 5143. In the example depicted, the arm unit 5145 includes joint portions 5147a, 5147b and 5147c and links 5149a and 5149b and is driven under the control of an arm controlling apparatus 5159. The endoscope 5115 is supported by the arm unit 5145 such that the position and the posture of the endoscope 5115 are controlled. Consequently, stable fixation in position of the endoscope 5115 can be implemented.

(Endoscope)

The endoscope 5115 includes the lens barrel 5117 which has a region of a predetermined length from a distal end thereof to be inserted into a body lumen of the patient 5185, and a camera head 5119 connected to a proximal end of the lens barrel 5117. In the example depicted, the endoscope 5115 is depicted which is configured as a hard mirror having the lens barrel 5117 of the hard type. However, the endoscope 5115 may otherwise be configured as a soft mirror having the lens barrel 5117 of the soft type.

The lens barrel 5117 has, at a distal end thereof, an opening in which an objective lens is fitted. A light source apparatus 5157 is connected to the endoscope 5115 such that light generated by the light source apparatus 5157 is introduced to a distal end of the lens barrel 5117 by a light guide extending in the inside of the lens barrel 5117 and is applied toward an observation target in a body lumen of the patient 5185 through the objective lens. It is to be noted that the endoscope 5115 may be a direct view mirror or may be a perspective view mirror or a side view mirror.

An optical system and an image pickup element are provided in the inside of the camera head 5119 such that reflected light (observation light) from an observation target is condensed on the image pickup element by the optical system. The observation light is photo-electrically converted by the image pickup element to generate an electric signal corresponding to the observation light, namely, an image signal corresponding to an observation image. The image signal is transmitted as RAW data to a CCU 5153. It is to be noted that the camera head 5119 has a function incorporated therein for suitably driving the optical system of the camera head 5119 to adjust the magnification and the focal distance.

It is to be noted that, in order to establish compatibility with, for example, a stereoscopic vision (3D display), a plurality of image pickup elements may be provided on the camera head 5119. In this case, a plurality of relay optical systems are provided in the inside of the lens barrel 5117 in order to guide observation light to the plurality of respective image pickup elements.

(Various Apparatus Incorporated in Cart)

The CCU 5153 includes a central processing unit (CPU), a graphics processing unit (GPU) or the like and integrally controls operation of the endoscope 5115 and the display apparatus 5155. Specifically, the CCU 5153 performs, for an image signal received from the camera head 5119, various image processes for displaying an image based on the image signal such as, for example, a development process (demosaic process). The CCU 5153 provides the image signal for which the image processes have been performed to the display apparatus 5155. Further, the audiovisual controller 5107 depicted in FIG. B1 is connected to the CCU 5153. The CCU 5153 provides the image signal for which the image processes have been performed also to the audiovisual controller 5107. Further, the CCU 5153 transmits a control signal to the camera head 5119 to control driving of the camera head 5119. The control signal may include information relating to an image pickup condition such as a magnification or a focal distance. The information relating to an image pickup condition may be inputted through the inputting apparatus 5161 or may be inputted through the centralized operation panel 5111 described hereinabove.

The display apparatus 5155 displays an image based on an image signal for which the image processes have been performed by the CCU 5153 under the control of the CCU 5153. If the endoscope 5115 is ready for imaging of a high resolution such as 4K (horizontal pixel number 3840× vertical pixel number 2160), 8K (horizontal pixel number 7680×vertical pixel number 4320) or the like and/or ready for 3D display, then a display apparatus by which corresponding display of the high resolution and/or 3D display are possible may be used as the display apparatus 5155. Where the apparatus is ready for imaging of a high resolution such as 4K or 8K, if the display apparatus used as the display apparatus 5155 has a size of equal to or not less than 55 inches, then a more immersive experience can be obtained. Further, a plurality of display apparatus 5155 having different resolutions and/or different sizes may be provided in accordance with purposes.

The light source apparatus 5157 includes a light source such as, for example, a light emitting diode (LED) and supplies irradiation light for imaging of a surgical region to the endoscope 5115.

The arm controlling apparatus 5159 includes a processor such as, for example, a CPU and operates in accordance with a predetermined program to control driving of the arm unit 5145 of the supporting arm apparatus 5141 in accordance with a predetermined controlling method.

An inputting apparatus 5161 is an input interface for the endoscopic surgery system 5113. A user can perform inputting of various kinds of information or instruction inputting to the endoscopic surgery system 5113 through the inputting apparatus 5161. For example, the user would input various kinds of information relating to surgery such as physical information of a patient, information regarding a surgical procedure of the surgery and so forth through the inputting apparatus 5161. Further, the user would input, for example, an instruction to drive the arm unit 5145, an instruction to change an image pickup condition (type of irradiation light, magnification, focal distance or the like) by the endoscope 5115, an instruction to drive the energy treatment tool 5135 or a like through the inputting apparatus 5161.

The type of the inputting apparatus 5161 is not limited and may be that of any one of various known inputting apparatus. As the inputting apparatus 5161, for example, a mouse, a keyboard, a touch panel, a switch, a foot switch 5171 and/or a lever or the like may be applied. Where a touch panel is used as the inputting apparatus 5161, it may be provided on the display face of the display apparatus 5155.

The inputting apparatus 5161 is otherwise a device to be mounted on a user such as, for example, a glasses type wearable device or a head mounted display (HMD), and various kinds of inputting are performed in response to a gesture or a line of sight of the user detected by any of the devices mentioned. Further, the inputting apparatus 5161 includes a camera which can detect a motion of a user, and various kinds of inputting are performed in response to a gesture or a line of sight of a user detected from a video picked up by the camera. Further, the inputting apparatus 5161 includes a microphone which can collect the voice of a user, and various kinds of inputting are performed by voice through the microphone. By configuring the inputting apparatus 5161 such that various kinds of information can be inputted in a contactless fashion in this manner, especially a user who belongs to a clean area (for example, the surgeon 5181) can operate an apparatus belonging to an unclean area in a contactless fashion. Further, since the user can operate an apparatus without releasing a possessed surgical tool from its hand, the convenience to the user is improved.

A treatment tool controlling apparatus 5163 controls driving of the energy treatment tool 5135 for cautery or incision of a tissue, sealing of a blood vessel or the like. A pneumoperitoneum apparatus 5165 feeds gas into a body lumen of the patient 5185 through the pneumoperitoneum tube 5133 to inflate the body lumen in order to secure the field of view of the endoscope 5115 and secure the working space for the surgeon. A recorder 5167 is an apparatus capable of recording various kinds of information relating to surgery. A printer 5169 is an apparatus capable of printing various kinds of information relating to surgery in various forms such as a text, an image or a graph.

In the following, especially a characteristic configuration of the endoscopic surgery system 5113 is described in more detail.

(Supporting Arm Apparatus)

The supporting arm apparatus 5141 includes the base unit 5143 serving as a base, and the arm unit 5145 extending from the base unit 5143. In the example depicted, the arm unit 5145 includes the plurality of joint portions 5147a, 5147b and 5147c and the plurality of links 5149a and 5149b connected to each other by the joint portion 5147b. In FIG. 16, for simplified illustration, the configuration of the arm unit 5145 is depicted in a simplified form. Actually, the shape, number and arrangement of the joint portions 5147a to 5147c and the links 5149a and 5149b and the direction and so forth of axes of rotation of the joint portions 5147a to 5147c can be set suitably such that the arm unit 5145 has a desired degree of freedom. For example, the arm unit 5145 may preferably be included such that it has a degree of freedom equal to or not less than 6 degrees of freedom. This makes it possible to move the endoscope 5115 freely within the movable range of the arm unit 5145. Consequently, it becomes possible to insert the lens barrel 5117 of the endoscope 5115 from a desired direction into a body lumen of the patient 5185.

An actuator is provided in the joint portions 5147a to 5147c, and the joint portions 5147a to 5147c include such that they are rotatable around predetermined axes of rotation thereof by driving of the actuator. The driving of the actuator is controlled by the arm controlling apparatus 5159 to control the rotational angle of each of the joint portions 5147a to 5147c thereby to control driving of the arm unit 5145. Consequently, control of the position and the posture of the endoscope 5115 can be implemented. Thereupon, the arm controlling apparatus 5159 can control driving of the arm unit 5145 by various known controlling methods such as force control or position control.

For example, if the surgeon 5181 suitably performs operation inputting through the inputting apparatus 5161 (including the foot switch 5171), then driving of the arm unit 5145 may be controlled suitably by the arm controlling apparatus 5159 in response to the operation input to control the position and the posture of the endoscope 5115. After the endoscope 5115 at the distal end of the arm unit 5145 is moved from an arbitrary position to a different arbitrary position by the control just described, the endoscope 5115 can be supported fixedly at the position after the movement. It is to be noted that the arm unit 5145 may be operated in a master-slave fashion. In this case, the arm unit 5145 may be remotely controlled by the user through the inputting apparatus 5161 which is placed at a place remote from the surgery room.

Further, where force control is applied, the arm controlling apparatus 5159 may perform power-assisted control to drive the actuators of the joint portions 5147a to 5147c such that the arm unit 5145 may receive external force by the user and move smoothly following the external force. This makes it possible to move the arm unit 5145 with comparatively weak force when the user directly touches with and moves the arm unit 5145. Accordingly, it becomes possible for the user to move the endoscope 5115 more intuitively by a simpler and easier operation, and the convenience to the user can be improved.

Here, generally in endoscopic surgery, the endoscope 5115 is supported by a medical doctor called scopist. In contrast, where the supporting arm apparatus 5141 is used, the position of the endoscope 5115 can be fixed with a higher degree of certainty without hands, and therefore, an image of a surgical region can be obtained stably and surgery can be performed smoothly.

It is to be noted that the arm controlling apparatus 5159 may not necessarily be provided on the cart 5151. Further, the arm controlling apparatus 5159 may not necessarily be a single apparatus. For example, the arm controlling apparatus 5159 may be provided in each of the joint portions 5147a to 5147c of the arm unit 5145 of the supporting arm apparatus 5141 such that the plurality of arm controlling apparatus 5159 cooperate with each other to implement driving control of the arm unit 5145.

(Light Source Apparatus)

The light source apparatus 5157 supplies irradiation light upon imaging of a surgical region to the endoscope 5115. The light source apparatus 5157 includes a white light source which includes, for example, an LED, a laser light source or a combination of them. In this case, where a white light source includes a combination of red, green, and blue (RGB) laser light sources, since the output intensity and the output timing can be controlled with a high degree of accuracy for each color (each wavelength), adjustment of the white balance of a picked up image can be performed by the light source apparatus 5157. Further, in this case, if laser beams from the RGB laser light sources are applied time-divisionally on an observation target and driving of the image pickup elements of the camera head 5119 is controlled in synchronism with the irradiation timings, then images individually corresponding to the R, G and B colors can be picked up time-divisionally. According to the method just described, a color image can be obtained even if a color filter is not provided for the image pickup element.

Further, driving of the light source apparatus 5157 may be controlled such that the intensity of light to be outputted is changed for each predetermined time. By controlling driving of the image pickup element of the camera head 5119 in synchronism with the timing of the change of the intensity of light to acquire images time-divisionally and synthesizing the images, an image of a high dynamic range free from underexposed blocked up shadows and overexposed highlights can be created.

Further, the light source apparatus 5157 may be configured to supply light of a predetermined wavelength band ready for special light observation. In special light observation, for example, by utilizing the wavelength dependency of absorption of light of a body tissue, narrow band light observation (narrow band imaging) of imaging a predetermined tissue such as a blood vessel of a superficial portion of the mucous membrane or the like in a high contrast is performed by applying light of a narrower band in comparison with irradiation light upon ordinary observation (namely, white light). Alternatively, in special light observation, fluorescent observation for obtaining an image from fluorescent light generated by irradiation of excitation light may also be performed. In fluorescent observation, it is possible to perform observation of fluorescent light from a body tissue by irradiating excitation light on the body tissue (autofluorescence observation) or to obtain a fluorescent light image by locally injecting a reagent such as indocyanine green (ICG) into a body tissue and irradiating excitation light corresponding to a fluorescent light wavelength of the reagent upon the body tissue. The light source apparatus 5157 can be configured to supply such narrow-band light and/or excitation light suitable for special light observation as described above.

(Camera Head and CCU)

Figure 17:
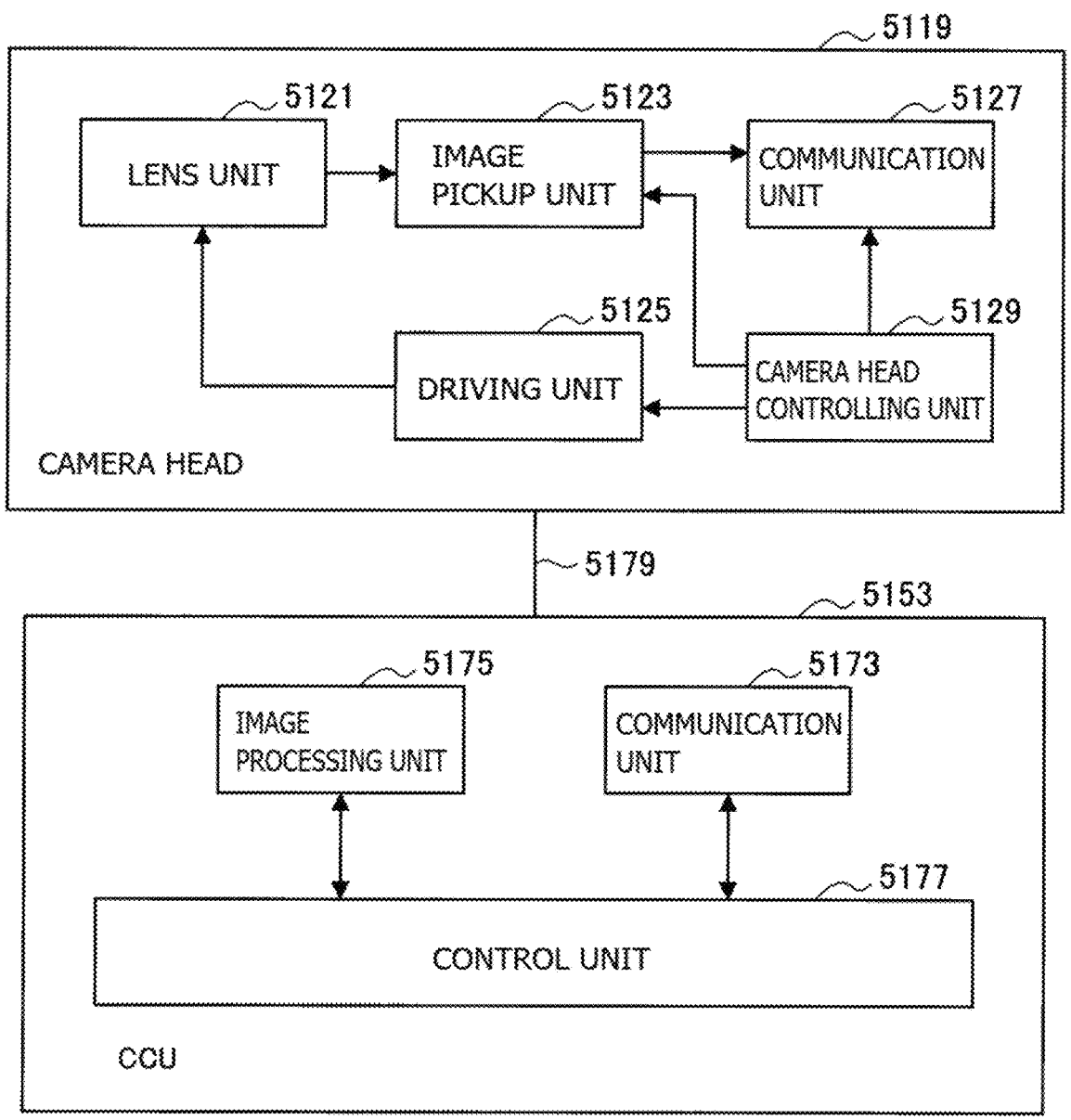
FIG. 17 is a block diagram depicting an example of a functional configuration of a camera head and a camera control unit (CCU) depicted in FIG. 16.

Functions of the camera head 5119 of the endoscope 5115 and the CCU 5153 are described in more detail with reference to FIG. 17. FIG. 17 is a block diagram depicting an example of a functional configuration of the camera head 5119 and the CCU 5153 depicted in FIG. 16.

Referring to FIG. 17, the camera head 5119 has, as functions thereof, a lens unit 5121, an image pickup unit 5123, a driving unit 5125, a communication unit 5127 and a camera head controlling unit 5129. Further, the CCU 5153 has, as functions thereof, a communication unit 5173, an image processing unit 5175 and a control unit 5177. The camera head 5119 and the CCU 5153 are connected to be bidirectionally communicable to each other by a transmission cable 5179.

First, a functional configuration of the camera head 5119 is described. The lens unit 5121 is an optical system provided at a connecting location of the camera head 5119 to the lens barrel 5117. Observation light taken in from a distal end of the lens barrel 5117 is introduced into the camera head 5119 and enters the lens unit 5121. The lens unit 5121 includes a combination of a plurality of lenses including a zoom lens and a focusing lens. The lens unit 5121 has optical properties adjusted such that the observation light is condensed on a light receiving face of the image pickup element of the image pickup unit 5123. Further, the zoom lens and the focusing lens include such that the positions thereof on their optical axis are movable for adjustment of the magnification and the focal point of a picked up image.

The image pickup unit 5123 includes an image pickup element and disposed at a succeeding stage to the lens unit 5121. Observation light having passed through the lens unit 5121 is condensed on the light receiving face of the image pickup element, and an image signal corresponding to the observation image is generated by photoelectric conversion. The image signal generated by the image pickup unit 5123 is provided to the communication unit 5127.

As the image pickup element which is included by the image pickup unit 5123, an image sensor, for example, of the complementary metal oxide semiconductor (CMOS) type is used which has a Bayer array and is capable of picking up an image in color. It is to be noted that, as the image pickup element, an image pickup element may be used which is ready, for example, for imaging of an image of a high resolution equal to or not less than 4K. If an image of a surgical region is obtained in a high resolution, then the surgeon 5181 can comprehend a state of the surgical region in enhanced details and can proceed with the surgery more smoothly.

Further, the image pickup element which is included by the image pickup unit 5123 is configured such that it has a pair of image pickup elements for acquiring image signals for the right eye and the left eye compatible with 3D display. Where 3D display is applied, the surgeon 5181 can comprehend the depth of a living body tissue in the surgical region with a higher degree of accuracy. It is to be noted that, if the image pickup unit 5123 is configured as that of the multi-plate type, then a plurality of systems of lens units 5121 are provided corresponding to the individual image pickup elements of the image pickup unit 5123.

The image pickup unit 5123 may not necessarily be provided on the camera head 5119. For example, the image pickup unit 5123 may be provided just behind the objective lens in the inside of the lens barrel 5117.

The driving unit 5125 includes an actuator and moves the zoom lens and the focusing lens of the lens unit 5121 by a predetermined distance along the optical axis under the control of the camera head controlling unit 5129. Consequently, the magnification and the focal point of a picked up image by the image pickup unit 5123 can be adjusted suitably.

The communication unit 5127 includes a communication apparatus for transmitting and receiving various kinds of information to and from the CCU 5153. The communication unit 5127 transmits an image signal acquired from the image pickup unit 5123 as RAW data to the CCU 5153 through the transmission cable 5179. Thereupon, in order to display a picked up image of a surgical region in low latency, preferably the image signal is transmitted by optical communication. This is because, since, upon surgery, the surgeon 5181 performs surgery while observing the state of an affected area through a picked up image, in order to achieve surgery with a higher degree of safety and certainty, it is demanded for a moving image of the surgical region to be displayed on the real time basis as far as possible. Where optical communication is applied, a photoelectric conversion module for converting an electric signal into an optical signal is provided in the communication unit 5127. After the image signal is converted into an optical signal by the photoelectric conversion module, it is transmitted to the CCU 5153 through the transmission cable 5179.

Further, the communication unit 5127 receives a control signal for controlling driving of the camera head 5119 from the CCU 5153. The control signal includes information relating to image pickup conditions such as, for example, information that a frame rate of a picked up image is designated, information that an exposure value upon image picking up is designated and/or information that a magnification and a focal point of a picked up image are designated. The communication unit 5127 provides the received control signal to the camera head controlling unit 5129. It is to be noted that also the control signal from the CCU 5153 may be transmitted by optical communication. In this case, a photoelectric conversion module for converting an optical signal into an electric signal is provided in the communication unit 5127. After the control signal is converted into an electric signal by the photoelectric conversion module, it is provided to the camera head controlling unit 5129.

It is to be noted that the image pickup conditions such as the frame rate, exposure value, magnification or focal point are set automatically by the control unit 5177 of the CCU 5153 on the basis of an acquired image signal. In other words, an auto exposure (AE) function, an auto focus (AF) function and an auto white balance (AWB) function are incorporated in the endoscope 5115.

The camera head controlling unit 5129 controls driving of the camera head 5119 on the basis of a control signal from the CCU 5153 received through the communication unit 5127. For example, the camera head controlling unit 5129 controls driving of the image pickup element of the image pickup unit 5123 on the basis of information that a frame rate of a picked up image is designated and/or information that an exposure value upon image picking up is designated. Further, for example, the camera head controlling unit 5129 controls the driving unit 5125 to suitably move the zoom lens and the focus lens of the lens unit 5121 on the basis of information that a magnification and a focal point of a picked up image are designated. The camera head controlling unit 5129 may include a function for storing information for identifying of the lens barrel 5117 and/or the camera head 5119.

It is to be noted that, by disposing the components such as the lens unit 5121 and the image pickup unit 5123 in a sealed structure having high airtightness and high waterproof, the camera head 5119 can be provided with resistance to an autoclave sterilization process.

Now, a functional configuration of the CCU 5153 is described. The communication unit 5173 includes a communication apparatus for transmitting and receiving various kinds of information to and from the camera head 5119. The communication unit 5173 receives an image signal transmitted thereto from the camera head 5119 through the transmission cable 5179. Thereupon, the image signal may be transmitted preferably by optical communication as described above. In this case, for the compatibility with optical communication, the communication unit 5173 includes a photoelectric conversion module for converting an optical signal into an electric signal. The communication unit 5173 provides the image signal after conversion into an electric signal to the image processing unit 5175.

Further, the communication unit 5173 transmits, to the camera head 5119, a control signal for controlling driving of the camera head 5119. Also the control signal may be transmitted by optical communication.

The image processing unit 5175 performs various image processes for an image signal in the form of RAW data transmitted thereto from the camera head 5119. The image processes include various known signal processes such as, for example, a development process, an image quality improving process (a bandwidth enhancement process, a super-resolution process, a noise reduction (NR) process and/or an image stabilization process) and/or an enlargement process (electronic zooming process). Further, the image processing unit 5175 performs a detection process for an image signal for performing AE, AF and AWB.

The image processing unit 5175 includes a processor such as a CPU or a GPU, and when the processor operates in accordance with a predetermined program, the image processes and the detection process described above can be performed. It is to be noted that, where the image processing unit 5175 includes a plurality of GPUs, the image processing unit 5175 suitably divides information relating to an image signal such that image processes are performed in parallel by the plurality of GPUs.

The control unit 5177 performs various kinds of control relating to image picking up of a surgical region by the endoscope 5115 and display of the picked up image. For example, the control unit 5177 generates a control signal for controlling driving of the camera head 5119. Thereupon, if image pickup conditions are inputted by the user, then the control unit 5177 generates a control signal on the basis of the input by the user. Alternatively, where the endoscope 5115 has an AE function, an AF function and an AWB function incorporated therein, the control unit 5177 suitably calculates an optimum exposure value, focal distance and white balance in response to a result of a detection process by the image processing unit 5175 and generates a control signal.

Further, the control unit 5177 controls the display apparatus 5155 to display an image of a surgical region on the basis of an image signal for which the image processes have been performed by the image processing unit 5175. Thereupon, the control unit 5177 recognizes various objects in the surgical region image using various image recognition technologies. For example, the control unit 5177 can recognize a surgical tool such as forceps, a particular living body region, bleeding, mist when the energy treatment tool 5135 is used and so forth by detecting the shape, color and so forth of edges of the objects included in the surgical region image. The control unit 5177 causes, when it controls the display apparatus 5155 to display a surgical region image, various kinds of surgery supporting information to be displayed in an overlapping manner with an image of the surgical region using a result of the recognition. Where surgery supporting information is displayed in an overlapping manner and presented to the surgeon 5181, the surgeon 5181 can proceed with the surgery more safety and certainty.

The transmission cable 5179 which connects the camera head 5119 and the CCU 5153 to each other is an electric signal cable ready for communication of an electric signal, an optical fiber ready for optical communication or a composite cable thereof.

Here, while, in the example depicted in the figure, communication is performed by wired communication using the transmission cable 5179, the communication between the camera head 5119 and the CCU 5153 may be performed otherwise by wireless communication. Where the communication between the camera head 5119 and the CCU 5153 is performed by wireless communication, there is no necessity to lay the transmission cable 5179 in the surgery room. Therefore, such a situation that movement of medical staff in the surgery room is disturbed by the transmission cable 5179 can be eliminated.

An example of the surgery room system 5100 to which the technology according to an embodiment of the present disclosure can be applied has been described above. It is to be noted here that, although a case in which the medical system to which the surgery room system 5100 is applied is the endoscopic surgery system 5113 has been described as an example, the configuration of the surgery room system 5100 is not limited to that of the example described above. For example, the surgery room system 5100 may be applied to a soft endoscopic system for inspection or a microscopic surgery system in place of the endoscopic surgery system 5113.

The technology according to the present disclosure may be applied, in the above-described configurations, to the interface block that gives the image pickup instructions regarding each of the cameras making up the surgery room system 5100. Specifically, the interface including the video camera 100 and the picked-up image monitoring apparatus 200 explained above using FIGS. 1 to 13 may be employed in the interface block constituted by the camera head 5119 and the display unit 5155 in FIGS. 16 and 17 and by PCs (including tablets) through which medical staff such as doctors monitoring the surgery behind the surgeon 5181 or from outside the surgery room issue instructions and advice to the surgeon as well as to the operator of the centralized operation panel 5111. Utilization of the technology according to the present disclosure makes it possible to associate a particular position on the picked-up image with the display of the image pickup instructions such as the image pickup targeting instruction, zoom-in and zoom-out instructions, and pan instruction addressed to the camera operator of the camera head 5119 or the instructions and advice addressed to the surgeon 5181.

3. Alternative Examples

The above-described embodiment has indicated the example in which the picked-up image monitoring apparatus 200 transmits to the video camera 100 the data packet including the position information and the display information (ID) as the image pickup instruction information. Alternatively, the image pickup instruction information may conceivably be conveyed by voice from the picked-up image monitoring apparatus 200 to the video camera 100.

The above-described embodiment has also indicated the example in which the instruction type (mark, text) is displayed on the image position designated by the position information obtained in accordance with the user's operations on the touch panel of the picked-up image monitoring apparatus 200. In this case, if the position of the subject recognized by subject recognition (e.g., facial recognition or human body recognition) fails to match the position designated by the position information, position adjustment (including position information adjustment) may conceivably be performed in such a manner that the instruction type (mark, text) is displayed corresponding to the position of the recognized subject. This makes it possible, for example, to issue the image pickup targeting instruction to the camera operator more appropriately.

Whereas the above-described embodiment has further indicated the image pickup system including one video camera 100 and one picked-up image monitoring apparatus 200, there may conceivably be an image pickup system that includes multiple video cameras 100 and one picked-up image monitoring system 200, or an image pickup system that includes multiple units of either or both of the video camera 100 and the picked-up image monitoring apparatus 200.

Furthermore, whereas the above-described embodiment has indicated the example of the video camera 100 that integrates the image pickup unit 113 and the finder (display unit) 120, there may conceivably be a configuration in which the image pickup unit 113 is separated from the finder (display unit) 120. Likewise, whereas the above-described embodiment has indicated the example of the picked-up image monitoring apparatus 200 equipped integrally with the display panel (display unit) 216, there may conceivably a configuration in which the display panel (display unit) 216 is separately provided. Incidentally, the marks and texts indicative of the image pickup instructions for the above-described embodiment are only examples and are not limitative of the present disclosure.

The present disclosure may be implemented preferably in the following configurations:

(1)

An image processing apparatus including:

a transmission unit configured to transmit image data to external equipment;

a reception unit configured to receive instruction information regarding the image data from the external equipment; and a display-use image generating unit configured to generate a display-use image based on and reflecting the instruction information.

(2)

The image processing apparatus according to (1), in which the display-use image generating unit generates the display-use image by displaying details of the instruction information on an image corresponding to the image data.

(3)

The image processing apparatus according to (1) or (2), in which position information is added to the instruction information; and the display-use image generating unit generates the display-use image by displaying details of the instruction information in an image position indicated by the position information.

(4)

The image processing apparatus as stated in any one of paragraphs (1) to (3), in which details of the instruction information include image pickup instruction information.

(5)

The image processing apparatus as stated in any one of paragraphs (1) to (4), in which the display-use image generating unit generates the display-use image having either a displayed mark or a displayed text corresponding to details of the instruction information.

(6)

The image processing apparatus according to (5), in which the display-use image generating unit has a conversion table for obtaining either the mark or the text based on the instruction information and corresponding to the details thereof.

(7)

The image processing apparatus as stated in any one of paragraphs (1) to (6), further including:

an image pickup unit configured to obtain the image data.

(8)

The image processing apparatus as stated in any one of paragraphs (1) to (7), further including:

a display unit configured to display the display-use image.

(9)

An image processing method including:

a step of causing a transmission unit to transmit image data to external equipment;

a step of causing a reception unit to receive instruction information regarding the image data from the external equipment; and a step of causing a display-use image generating unit to generate a display-use image based on and reflecting the instruction information.

(10)

An image processing apparatus including:

a reception unit configured to receive image data from external equipment;

a processing unit configured to generate instruction information regarding the image data; and a transmission unit configured to transmit the instruction information to the external equipment.

(11)

The image processing apparatus according to (10), in which details of the instruction information include image pickup instruction information.

(12)

The image processing apparatus according to (10) or (11), in which the processing unit has a conversion table for obtaining the instruction information based on an operation performed by a user.

(13)

The image processing apparatus according to (12), further including:

a table setting unit configured to set the conversion table.

(14)

The image processing apparatus as stated in any one of paragraphs (10) to (14), in which the processing unit further generates a display-use image based on and reflecting the instruction information.

(15)

The image processing apparatus according to (14), in which the processing unit generates the display-use image having either a displayed mark or a displayed text corresponding to details of the instruction information.

(16)

The image processing apparatus according to (15), in which the processing unit has a conversion table for obtaining either the mark or the text based on the instruction information and corresponding to the details thereof.

(17)

The image processing apparatus as stated in any one of paragraphs (14) to (16), further including:

a display unit configured to display the display-use image.

(18)

The image processing apparatus as stated in any one of paragraphs (10) to (17), in which the transmission unit, after transmitting predetermined instruction information to the external equipment, further transmits to the external equipment cancellation information giving an instruction to cancel the predetermined instruction information if a user performs an operation to cancel the predetermined cancellation information.

(19)

An image processing method including:

a step of causing a reception unit to receive image data from external equipment;

a step of causing a processing unit to generate instruction information regarding the image data; and a step of causing a transmission unit to transmit the instruction information to the external equipment.

(20)

An image processing system including:

an image pickup apparatus; and a picked-up image monitoring apparatus, in which the image pickup apparatus includes an image pickup unit configured to obtain moving image data by imaging a subject, a transmission unit configured to transmit image data corresponding to the moving image data to the picked-up image monitoring apparatus, a reception unit configured to receive instruction information regarding the image data from the picked-up image monitoring apparatus, a display-use image generating unit configured to generate display-use image based on and reflecting the instruction information, and a display unit configured to display the display-use image, and the picked-up image monitoring apparatus includes a reception unit configured to receive the image data from the image pickup apparatus, a display unit configured to display an image derived from the image data, a processing unit configured to generate instruction information regarding the image data, and a transmission unit configured to transmit the instruction information to the image pickup apparatus.

REFERENCE SIGNS LIST

10 . . . Image pickup system
100 . . . Video camera
111 . . . Control unit
112 . . . Operation inputting unit
113 . . . Image pickup unit
114 . . . Picked-up image signal processing unit
115 . . . Encoding unit
116 . . . Recording/reproducing unit
117 . . . Recording medium
118 . . . Communication unit
119 . . . Finder display processing unit
120 . . . Finder
200 . . . Picked-up image monitoring unit
211 . . . Control unit
212 . . . Operation inputting unit
213 . . . Communication unit
214 . . . Decoding unit
215 . . . Display processing unit
216 . . . Display panel

The invention claimed is:

1. An image processing apparatus, comprising:

circuitry configured to:

receive a correspondence table from an external equipment, wherein the correspondence table comprises a plurality of instruction details in association with a plurality of identification information, and each identification information of the plurality of identification information is associated with a user operation;

transmit image data to the external equipment;
receive instruction information regarding the image data from the external equipment, wherein the instruction information includes a first identification information of the plurality of identification information and position information;
obtain a first instruction detail of the plurality of instruction details from the correspondence table based on the first identification information,
wherein
the position information indicates an image position; and
generate a display-use image based on the instruction information, wherein
the generated display-use image includes the first instruction detail at the image position indicated by the position information.

2. The image processing apparatus according to claim 1, wherein the circuitry is further configured to control display of the first instruction detail of the instruction information on the generated display-use image corresponding to the image data.

3. The image processing apparatus according to claim 1, wherein
the first instruction detail includes image pickup instruction information, and
the first instruction detail comprises at least one of the user operation, a type of image pickup instruction, a color of display detail associated with the instruction information, a shape of the display detail associated with the instruction information, or a movement of the display detail associated with the instruction information.

4. The image processing apparatus according to claim 1, wherein the display-use image further includes at least one of a text or a mark corresponding to the first instruction detail.

5. The image processing apparatus according to claim 4, wherein the circuitry is further configured to obtain at least one of the text or the mark from the correspondence table based on the first identification information and the first instruction detail.

6. The image processing apparatus according to claim 4, wherein
the instruction information corresponds to a specific instruction, and
at least one of a color, a shape, or movement of at least one of the text or the mark indicates a type of the specific instruction.

7. The image processing apparatus according to claim 1, further comprising an imager configured to obtain the image data.

8. The image processing apparatus according to claim 1, further comprising a display screen configured to display the display-use image.

9. An image processing method, comprising:
receiving a correspondence table from an external equipment,
wherein
the correspondence table comprises a plurality of instruction details in association with a plurality of identification information, and
each identification information of the plurality of identification information is associated with a user operation;
transmitting image data to the external equipment;
receiving instruction information regarding the image data from the external equipment,
wherein the instruction information includes a first identification information of the plurality of identification information and position information;
obtaining a first instruction detail of the plurality of instruction details from the correspondence table based on the first identification information,
wherein
the position information indicates an image position; and
generating a display-use image based on the instruction information, wherein
the generated display-use image includes the first instruction detail at the image position indicated by the position information.

10. An image processing apparatus, comprising:
circuitry configured to:
receive image data from an external equipment;
select a correspondence table from a plurality of correspondence tables,
wherein
the correspondence table comprises instruction details with respect to a user operation, and
each user operation is associated with an identification number in the correspondence table;
generate first instruction information regarding the image data based on the selected correspondence table and the user operation, wherein the first instruction information includes the identification number associated with the instruction details, and position information that indicates an image position;
generate a display-use image based on the first instruction information, wherein
the generated display-use image includes the instruction details at the image position indicated by the position information; and
transmit the first instruction information to the external equipment.

11. The image processing apparatus according to claim 10, wherein
the instruction details of the first instruction information include image pickup instruction information, and
the instruction details comprises, with respect to the identification number, at least one of the user operation, a type of image pickup instruction, a color of display details associated with the first instruction information, a shape of display details associated with the first instruction information, or a movement of display details associated with the first instruction information.

12. The image processing apparatus according to claim 10, wherein the circuitry is further configured to obtain the position information based on the user operation on the image data.

13. The image processing apparatus according to claim 10, the circuitry is configured to modify the correspondence table.

14. The image processing apparatus according to claim 10, wherein the display-use image further includes at least one of a text or a mark corresponding to the instruction details of the first instruction information.

15. The image processing apparatus according to claim 14, wherein the circuitry is further configured to obtain at least one of the text or the mark from the correspondence table based on the identification number and the instruction details.

16. The image processing apparatus according to claim 10, further comprising a display panel configured to display the display-use image.

17. The image processing apparatus according to claim 10, wherein the circuitry is further configured to:
transmit second instruction information to the external equipment; and
transmit cancellation information to the external equipment after the transmission of the second instruction information, wherein
the cancellation information corresponds to a specific instruction to cancel the second instruction information, and
the cancellation information is transmitted based on the user operation to cancel the second instruction information.

18. An image processing method, comprising:
receiving image data from an external equipment;
selecting a correspondence table from a plurality of correspondence tables,
wherein
the correspondence table comprises instruction details with respect to a user operation, and
each user operation is associated with an identification number in the correspondence table;
generating instruction information regarding the image data based on the selected correspondence table and the user operation,
wherein the instruction information includes the identification number associated with the instruction details, and position information that indicates an image position;
generating a display-use image based on the instruction information, wherein
the generated display-use image includes the instruction details at the image position indicated by the position information; and
transmitting the instruction information to the external equipment.

19. An image processing system, comprising:
an image pickup apparatus; and
a picked-up image monitoring apparatus, wherein
the image pickup apparatus includes:
an imager configured to obtain moving image data, corresponding to a subject, by an imaging process; and
first circuitry configured to:
transmit specific image data corresponding to the moving image data to the picked-up image monitoring apparatus;
receive a correspondence table from the picked-up image monitoring apparatus;
receive instruction information regarding the specific image data from the picked-up image monitoring apparatus, wherein the instruction information includes identification information and position information;
obtain instruction details from the received correspondence table based on the identification information,
wherein
the correspondence table comprises the instruction details in association with the identification information, and
the position information indicates an image position;
generate a display-use image based on the instruction information, wherein
the generated display-use image includes the instruction details at the image position indicated by the position information; and
a display screen configured to display the display-use image, and
the picked-up image monitoring apparatus includes second circuitry configured to:
receive the specific image data from the image pickup apparatus;
display a specific image of the received specific image data;
select the correspondence table from a plurality of correspondence tables, wherein
the correspondence table comprises the instruction details with respect to a user operation, and
each user operation is associated with the identification information in the correspondence table;
generate the instruction information regarding the received specific image data based on the selected correspondence table and the user operation on the displayed specific image,
wherein the instruction information includes the identification information associated with the instruction details, and position information that indicates an image position; and
transmit the generated instruction information to the image pickup apparatus.

* * * * *